United States Patent
Yamada et al.

(10) Patent No.: US 11,445,763 B2
(45) Date of Patent: Sep. 20, 2022

(54) INHALATION COMPONENT GENERATION DEVICE, METHOD OF CONTROLLING INHALATION COMPONENT GENERATION DEVICE, AND PROGRAM

(71) Applicant: JAPAN TOBACCO INC., Tokyo (JP)

(72) Inventors: Manabu Yamada, Tokyo (JP); Manabu Takeuchi, Tokyo (JP); Takeshi Akao, Tokyo (JP); Takuma Nakano, Tokyo (JP); Hajime Fujita, Tokyo (JP)

(73) Assignee: JAPAN TOBACCO INC., Tokyo (JP)

(*) Notice: Subject to any disclaimer, the term of this patent is extended or adjusted under 35 U.S.C. 154(b) by 126 days.

(21) Appl. No.: 16/856,260

(22) Filed: Apr. 23, 2020

(65) Prior Publication Data

US 2020/0245688 A1 Aug. 6, 2020

Related U.S. Application Data

(63) Continuation of application No. PCT/JP2017/038223, filed on Oct. 23, 2017.

(51) Int. Cl.
*A24F 40/53* (2020.01)
*A24F 40/90* (2020.01)
(Continued)

(52) U.S. Cl.
CPC ............. *A24F 40/53* (2020.01); *A24F 40/50* (2020.01); *A24F 40/60* (2020.01); *A24F 40/90* (2020.01)

(58) Field of Classification Search
None
See application file for complete search history.

(56) References Cited

U.S. PATENT DOCUMENTS

2008/0067979 A1  3/2008  Hayasaki
2009/0230117 A1  9/2009  Fernando et al.
(Continued)

FOREIGN PATENT DOCUMENTS

CN  105611847 A  5/2016
CN  106255428 A  12/2016
(Continued)

OTHER PUBLICATIONS

International Search Report and Written Opinion dated Nov. 28, 2017 for PCT/JP2017/038223 filed on Oct. 23, 2017, 6 pages including English Translation of the International Search Report.
(Continued)

*Primary Examiner* — Phu H Nguyen
(74) *Attorney, Agent, or Firm* — Xsensus LLP

(57) ABSTRACT

An inhalation component generation device includes a load configured to vaporize or atomize an inhalation component source with electric power from a power supply, a notification unit, and a control unit configured to acquire a value indicating a remaining amount of the power supply and acquire an operation request signal to the load to generate a command for operating the load. The control unit is configured to cause the notification unit to perform second notification when the value indicating the remaining amount of the power supply is less than a first threshold and equal to or more than a second threshold smaller than the first threshold. The control unit is configured to cause the notification unit to perform third notification when the value indicating the remaining amount of the power supply is less than the second threshold. The first threshold is changeable based on an algorithm. The control unit is configured to set the first threshold based on a value derived by performing a smoothing process by which a primary first threshold
(Continued)

derived by the algorithm approaches at least one of a plurality of the first thresholds that are previously changed.

14 Claims, 19 Drawing Sheets

(51) Int. Cl.
 *A24F 40/50* (2020.01)
 *A24F 40/60* (2020.01)

(56) References Cited

U.S. PATENT DOCUMENTS

| | | | |
|---|---|---|---|
| 2012/0296587 A1* | 11/2012 | Sugiyama | G01R 31/367 702/63 |
| 2013/0019887 A1 | 1/2013 | Liu | |
| 2013/0042865 A1 | 2/2013 | Monsees et al. | |
| 2014/0053856 A1 | 2/2014 | Liu | |
| 2015/0027223 A1 | 1/2015 | Kishimoto et al. | |
| 2015/0216233 A1 | 8/2015 | Sears et al. | |
| 2015/0272223 A1 | 10/2015 | Weigensberg et al. | |
| 2016/0205998 A1 | 7/2016 | Matsumoto et al. | |
| 2017/0047756 A1 | 2/2017 | Xiang | |
| 2017/0258135 A1 | 9/2017 | Yerkic-Husejnovic et al. | |
| 2017/0258136 A1 | 9/2017 | Hawes et al. | |

FOREIGN PATENT DOCUMENTS

| | | |
|---|---|---|
| CN | 106714288 A | 5/2017 |
| JP | 08-191502 A | 7/1996 |
| JP | 11-103334 A | 4/1999 |
| JP | 2008-72870 A | 3/2008 |
| JP | 2010-104310 A | 5/2010 |
| JP | 2011-53097 A | 3/2011 |
| JP | 2011-64646 A | 3/2011 |
| JP | 2011-515080 A | 5/2011 |
| JP | 2014-524313 A | 9/2014 |
| JP | 2017-511690 A | 4/2017 |
| WO | 2014/150942 A2 | 9/2014 |
| WO | 2015/046386 A1 | 4/2015 |
| WO | 2015/052513 A2 | 4/2015 |
| WO | 2015/073975 A1 | 5/2015 |
| WO | 2015/119918 A1 | 8/2015 |
| WO | 2015/155612 A2 | 10/2015 |
| WO | 2015/161502 A1 | 10/2015 |
| WO | 2015/165747 A1 | 11/2015 |

OTHER PUBLICATIONS

International Search Report and Written Opinion dated Nov. 28, 2017 for PCT/JP2017/038222 filed on Oct. 23, 2017, 14 pages including English Translation of the International Search Report.
International Search Report and Written Opinion dated Nov. 28, 2017 for PCT/JP2017/038224 filed on Oct. 23, 2017, 14 pages including English Translation of the International Search Report.
Chinese Office Action dated Dec. 1, 2020, in corresponding Chinese Patent Application No. 201780096214.5.
International Preliminary Report on Patentability and Written Opinion of the International Searching Authority dated Nov. 28, 2017 in International Application No. PCT/JP2017/038222, 9 pages. (Previously filed; submitting English translation only.).
Taiwanese Examiner Interview Summary dated Feb. 20, 2021, in corresponding Taiwanese Patent Application No. 106137923.
Office Action dated May 28, 2021, in corresponding Canadian patent Application No. 3079379, 6 pages.
Extended European Search Report dated Jun. 11, 2021, in corresponding European Patent Application No. 17929643.9.

* cited by examiner

INHALATION COMPONENT GENERATION DEVICE, METHOD OF CONTROLLING INHALATION COMPONENT GENERATION DEVICE, AND PROGRAM

CROSS REFERENCE TO RELATED APPLICATIONS

The present application is a continuation application of International Application No. PCT/JP2017/038223, filed on Oct. 23, 2017.

TECHNICAL FIELD

The present invention relates to an inhalation component generation device including a load configured to vaporize or atomize an inhalation component source with electric power from a power supply.

BACKGROUND ART

Instead of a cigarette, there has been proposed an inhalation component generation device (an electronic cigarette) used for tasting an inhalation component generated by vaporizing or atomizing a flavor source such as tobacco or an aerosol source with a load such as a heater (PTL 1 to PTL 8). Such an inhalation component generation device includes a load configured to vaporize or atomize a flavor source and/or an aerosol source, a power supply configured to supply electric power to the load, and a control unit configured to control the load and the power supply.

PTLs 2 to 7 each disclose an inhalation component generation device provided with an LED (a light-emitting diode). In particular, PTLs 4 to 7 each disclose that the number of light emitting elements (LED) in a lighting state or a lighting pattern of the light emitting element is changed according to a state of charge of the power supply, the lighting-emitting element being provided in the inhalation component generation device.

PTL 9 discloses that a control voltage value is set according to the degradation information of a power supply before a voltage of the power supply reaches a discharge termination voltage. The control unit performs a process for completing the discharge of the secondary battery when the voltage of the power supply is equal to lower than the control voltage value.

CITATION LIST

Patent Literature

PTL 1: International Publication No. WO 2015/165747
PTL 2: U.S. Patent No. 2013/0019887
PTL 3: International Publication No. WO 2015/046386
PTL 4: International Publication No. WO 2015/073975
PTL 5: U.S. Patent No. 2015/0272223
PTL 6: International Publication No. WO 2015/119918
PTL 7: International Publication No. WO 2015/161502
PTL 8: International Publication No. WO 2014/150942
PTL 9: Japanese Patent Laid-Open No. 2011-53097

SUMMARY OF INVENTION

A first feature provides an inhalation component generation device including a load configured to vaporize or atomize an inhalation component source with electric power from a power supply, a notification unit, and a control unit configured to acquire a value indicating a remaining amount of the power supply and acquire an operation request signal to the load to generate a command for operating the load, wherein the control unit is configured to cause the notification unit to perform second notification when the value indicating the remaining amount of the power supply is less than a first threshold and equal to or more than a second threshold smaller than the first threshold, the control unit is configured to cause the notification unit to perform third notification when the value indicating the remaining amount of the power supply is less than the second threshold, the first threshold is changeable based on an algorithm, and the control unit is configured to set the first threshold based on a value derived by performing a smoothing process by which a primary first threshold derived by the algorithm approaches at least one of a plurality of the first thresholds that are previously changed.

The second feature provides the inhalation component generation device according to the first feature, wherein an intensity of the smoothing process is changed based on the number of the first thresholds that are previously changed.

The third feature provides the inhalation component generation device according to the first feature or the second feature, wherein the number of the first thresholds used for the smoothing process is changed based on the number of the first thresholds that are previously changed.

The fourth feature provides the inhalation component generation device according to any one of the first feature to the third feature, wherein the control unit is capable of acquiring a state of health of the power supply, and the intensity of the smoothing process is changed based on the state of health.

The fifth feature provides the inhalation component generation device according to the fourth feature, wherein the number of the first thresholds used for the smoothing process is changed based on the state of health.

The sixth feature provides the inhalation component generation device according to the fourth feature or the fifth feature, wherein the intensity of the smoothing process is weakened as the state of health progresses.

The seventh feature provides the inhalation component generation device according to any one of the fourth feature to the sixth feature, wherein the control unit sets the first threshold to a primary first threshold derived by the predetermined algorithm when the state of health has progressed beyond a predetermined determination state.

The eighth feature provides the inhalation component generation device according to any one of the fourth feature to the seventh feature, wherein the control unit is capable of acquiring a state of health of the power supply, and the intensity of the smoothing process is changed based on the number of the first thresholds that are previously changed and the state of health weighted by the number of the first thresholds.

The ninth feature provides the inhalation component generation device according to the eighth feature, wherein the number of the first thresholds used in the smoothing process is changed based on the number of the first thresholds that are previously changed and the state of health weighted by the number of the first thresholds.

The tenth feature provides the inhalation component generation device according to any one of the first feature to the ninth feature, wherein the control unit detects degradation or abnormalities of the power supply when the set first threshold is equal to or more than a predetermined determination value.

The eleventh feature provides the inhalation component generation device according to the tenth feature, wherein the control unit controls the notification unit to perform fourth notification when the degradation or abnormality of the power supply has been detected.

The twelfth feature provides the inhalation component generation device according to any one of the first feature to the eleventh feature, further including a connection unit capable of electrically disconnecting and connecting the load from/to the power supply, wherein the control unit uses only the first threshold obtained after the load is attached to the connection unit in the smoothing process.

The thirteenth feature provides the inhalation component generation device according to any one of the first feature to the twelfth feature, further including a memory configured to store a history of the first threshold, and a connection unit capable of electrically disconnecting and connecting the load from/to the power supply, wherein the control unit disables or deletes at least a part of the first thresholds stored in the memory based on attachment and detachment of the load to and from the connection unit.

The fourteenth feature provides the inhalation component generation device according to any one of the first feature to the thirteenth feature, wherein the control unit changes the first threshold when a value indicating a remaining amount of the power supply is equal to or less than the second threshold or the power supply is charged.

The fifteenth feature provides a method of controlling an inhalation component generation device including a load configured to vaporize or atomize an inhalation component source with electric power from a power supply, the method including the steps of acquiring a value indicating a remaining amount of the power supply, issuing second notification when the value indicating the remaining amount of the power supply acquired in the step of acquiring is less than a first threshold and equal to or more than a second threshold smaller than the first threshold, issuing third notification when the value indicating the remaining amount of the power supply acquired in the step of acquiring is less than the second threshold, and setting the first threshold based on a value obtained by performing a smoothing process by which a primary first threshold derived by an algorithm approaches at least one of a plurality of the first thresholds that are previously changed.

The sixteenth feature provides a program causing an inhalation component generation device to execute the method according to the fifteenth feature.

DESCRIPTION OF EMBODIMENTS

Figure 1:
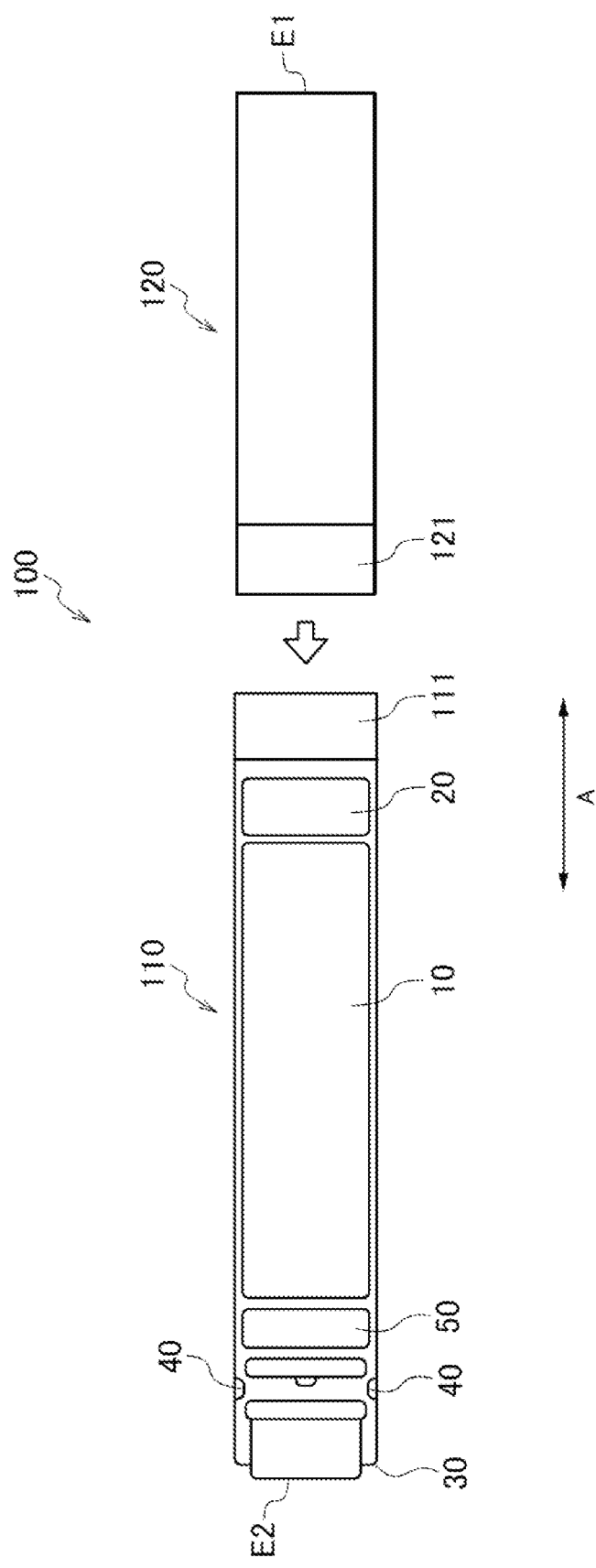
FIG. 1 is a schematic diagram illustrating an inhalation component generation device according to one embodiment.

Hereinafter, embodiments will be described. Note that the same or similar parts are denoted by the same or similar reference signs in the description of the drawings below. However, it should be noted that the drawings are schematic and ratios in dimensions may be different from actual ones.

Therefore, specific dimensions and the like should be determined with reference to the following description. Moreover, it is a matter of course that parts having different dimensional relationships and ratios may be included between the mutual drawings.

[Outline of Disclosure]

PTL 9 discloses that a control voltage value is set according to the degradation information of the secondary battery before the voltage of the power supply reaches the discharge termination voltage. This control voltage value is used as an index for completing the discharge of the secondary battery. This control voltage value is set based on the degradation information of the secondary battery, but it is difficult to accurately calculate the degradation information of the secondary battery. Therefore, the calculation value of the degradation information of the secondary battery may greatly vary every time the degradation information is calculated. Thus, it is not preferable to control the device based on the value that may vary every time the degradation information is calculated.

According to one aspect, an inhalation component generation device includes a load configured to vaporize or atomize an inhalation component source with electric power from a power supply, a notification unit, and a control unit configured to acquire a value indicating a remaining amount of the power supply and acquire an operation request signal to the load to generate a command for operating the load. The control unit is configured to cause the notification unit to perform second notification when the value indicating the remaining amount of the power supply is less than a first threshold and equal to or more than a second threshold smaller than the first threshold. Furthermore, the control unit is configured to cause the notification unit to perform third notification when the value indicating the remaining amount of the power supply is less than the second threshold. The first threshold may be changed based on an algorithm. The control unit is configured to set the first threshold based on a value derived by performing a smoothing process by which a primary first threshold derived by the algorithm approaches at least one of a plurality of the first thresholds that are previously changed.

According to this aspect, the above-described first threshold is set based on a value derived by performing the smoothing process of approaching at least one of the plurality of first thresholds that are previously changed. Therefore, even when the accuracy of the primary first threshold derived by the above-described algorithm is not satisfactory, the first threshold variation can be reduced by performing the smoothing process. Accordingly, this can inhibit the second notification from being made to a user at an undesirable timing due to the variation in the derived primary first threshold, so that an unnatural feel sensed by the user can be prevented.

First Embodiment (Inhalation Component Generation Device)

Figure 2:
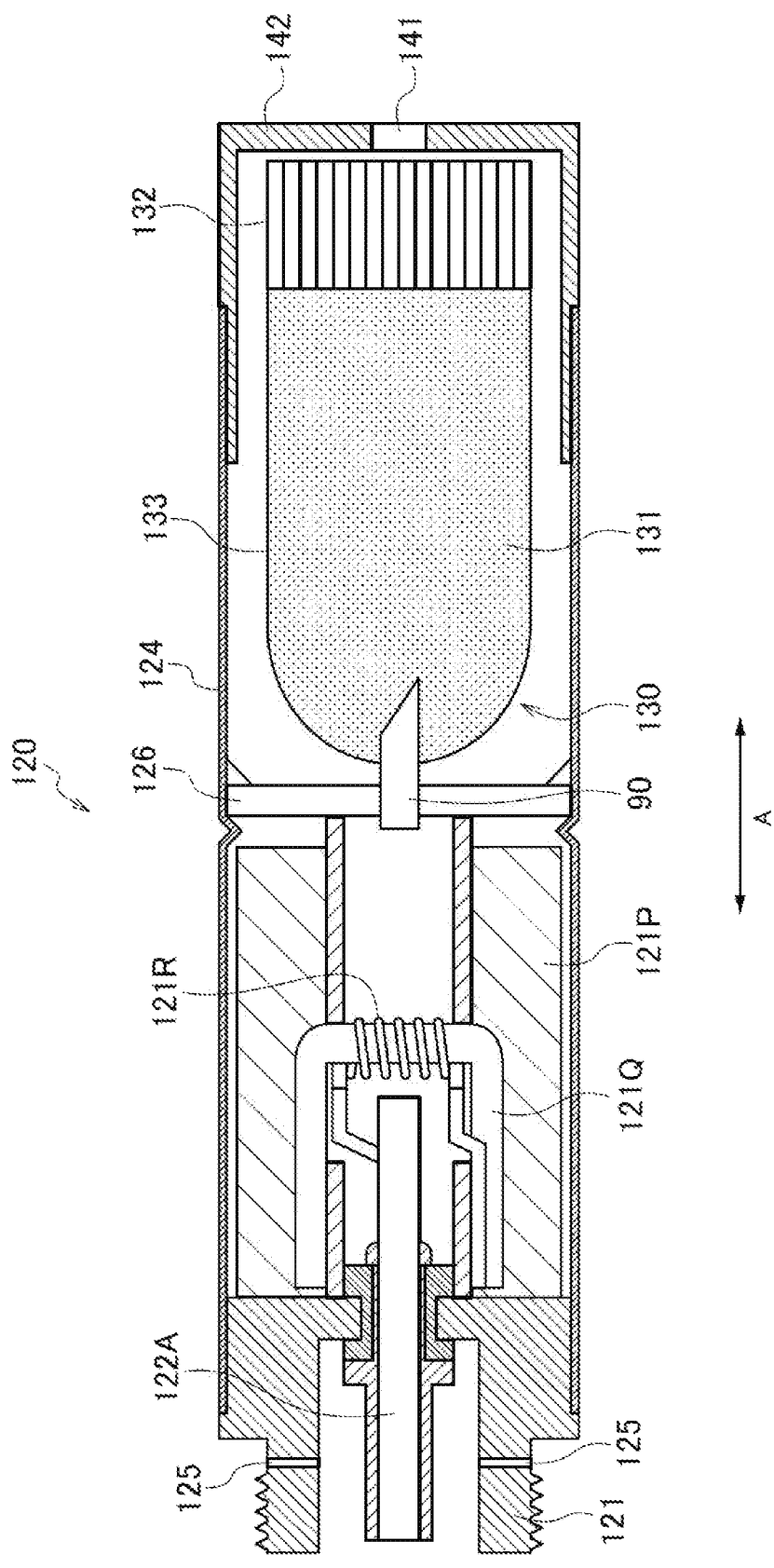
FIG. 2 is a diagram illustrating an atomizing unit according to one embodiment.
Figure 3:
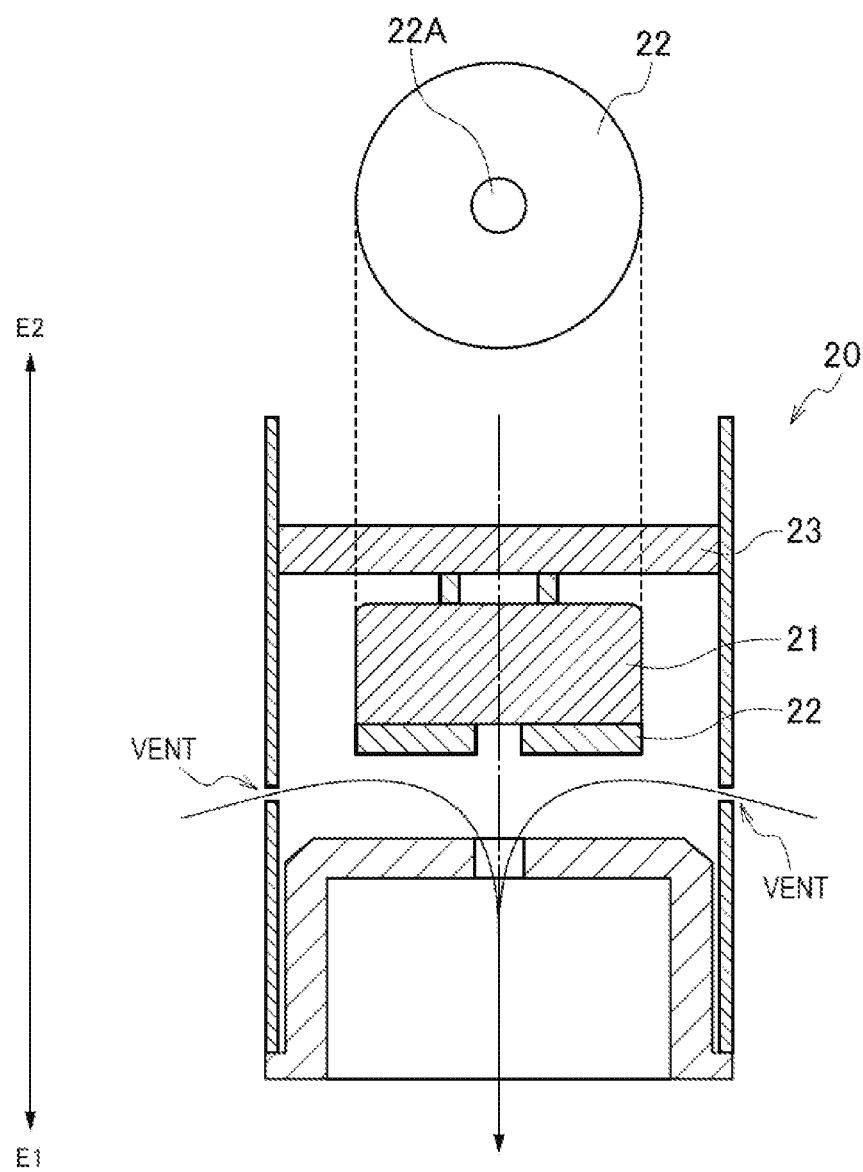
FIG. 3 is a schematic diagram illustrating an example of a configuration of an inhalation sensor according to one embodiment.
Figure 4:
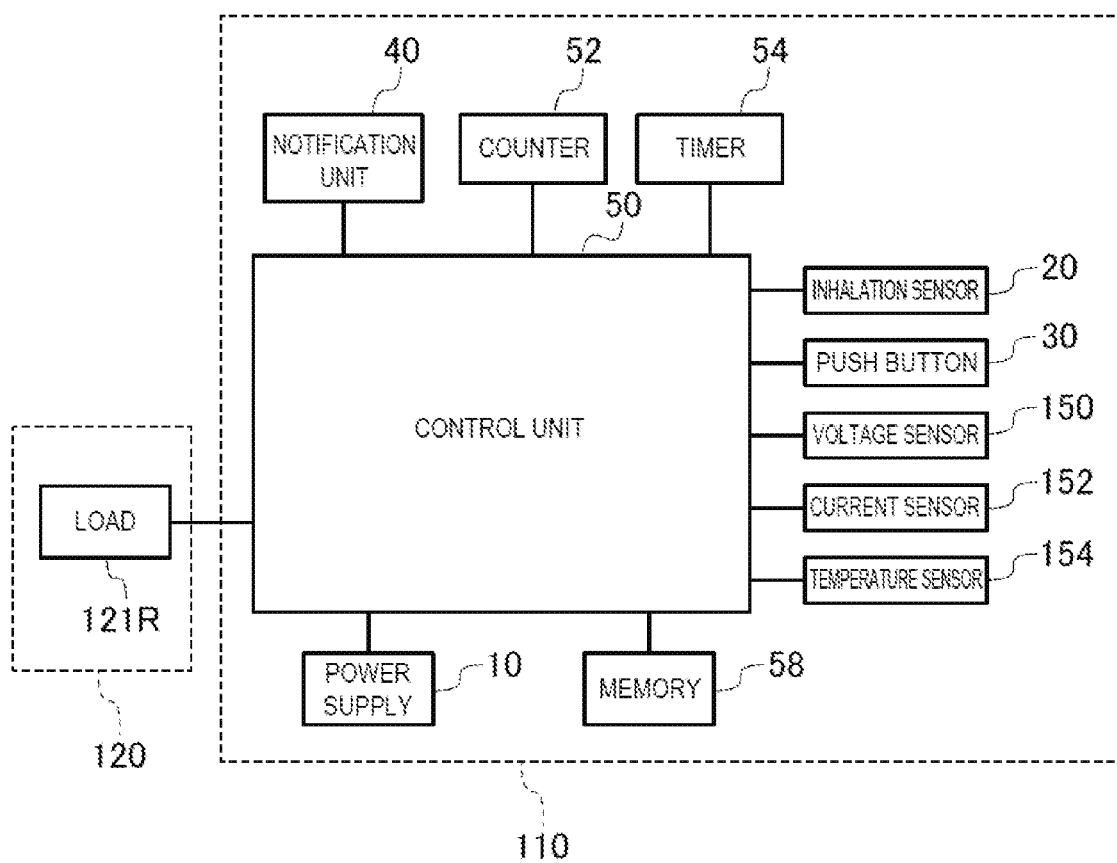
FIG. 4 is a block diagram illustrating the inhalation component generation device.
Figure 5:
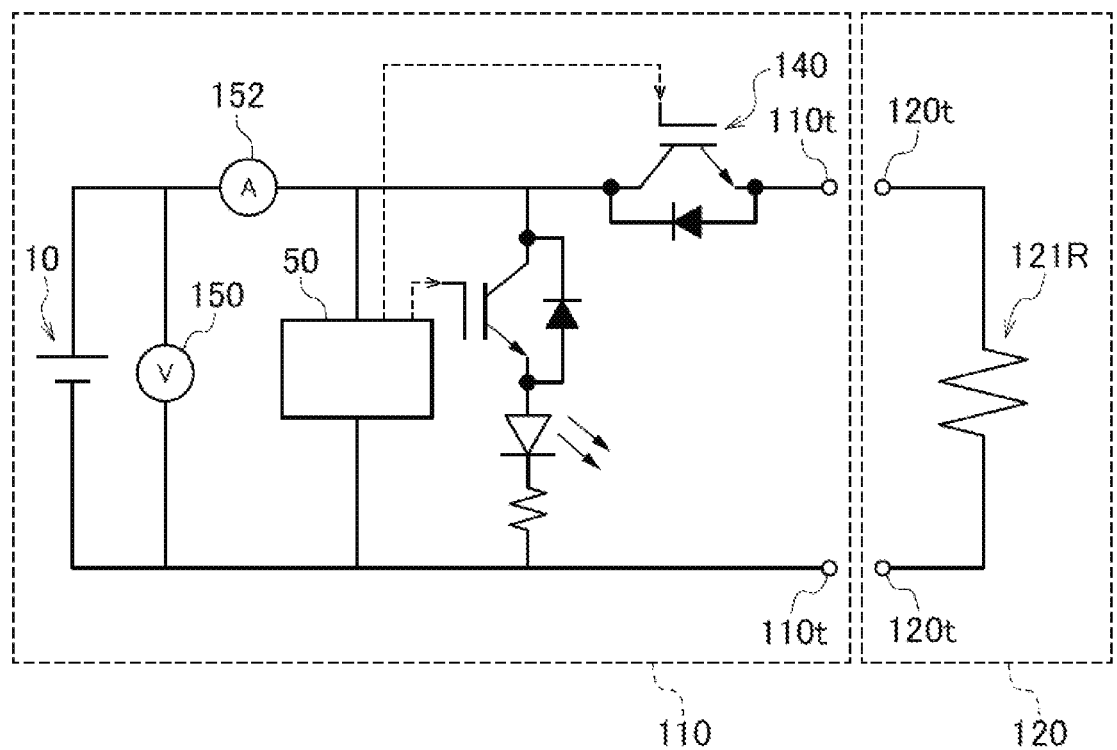
FIG. 5 is a diagram illustrating an electrical circuit of the atomizing unit and an electrical unit in a state in which a load is connected.
Figure 6:
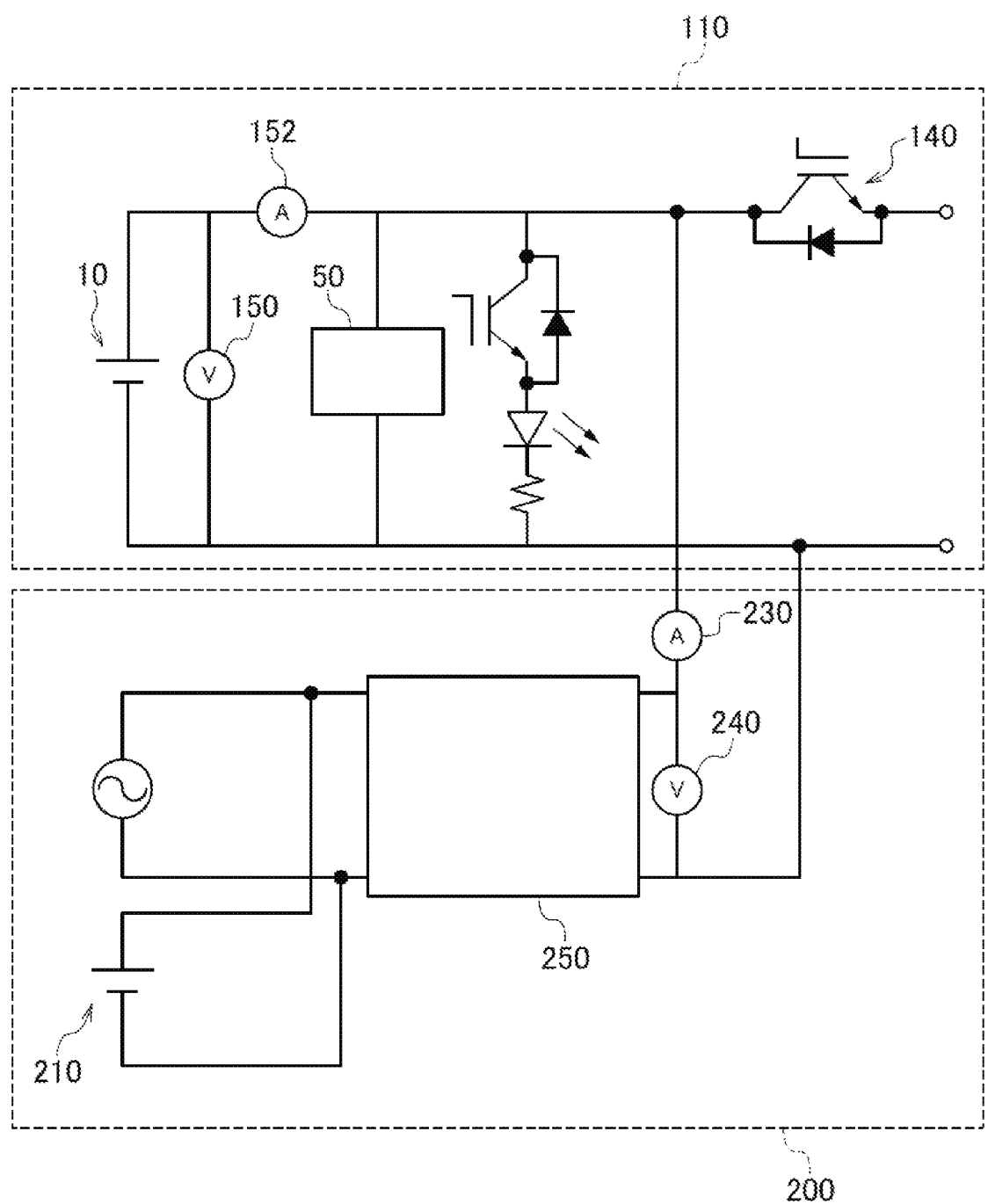
FIG. 6 is a diagram illustrating an electrical circuit of a charger and the electrical unit in a state in which a charger is connected.

Hereinafter, an inhalation component generation device according to a first embodiment will be described. FIG. 1 is an exploded view illustrating an inhalation component generation device according to one embodiment. FIG. 2 is a diagram illustrating an atomizing unit according to one embodiment. FIG. 3 is a schematic diagram illustrating an example of a configuration of an inhalation sensor according to one embodiment. FIG. 4 is a block diagram illustrating the inhalation component generation device. FIG. 5 is a diagram illustrating an electrical circuit of the atomizing unit and an electrical unit in a state in which a load is connected. FIG. 6 is a diagram illustrating an electrical circuit of a charger and the electrical unit in a state in which a charger is connected.

An inhalation component generation device 100 may be a non-combustion-type flavor inhaler for inhaling an inhalation component (an inhaling flavor component) without combustion. The inhalation component generation device 100 may have a shape extending along a predetermined direction A which is a direction from a non-inhalation port end E2 toward an inhalation port end E1. In this case, the inhalation component generation device 100 may include one end E1 having an inhalation port 141 for inhaling an inhalation component and the other end E2 opposite to the inhalation port 141.

The inhalation component generation device 100 may include an electrical unit 110 and an atomizing unit 120. The atomizing unit 120 may be configured to be detachably attached to the electrical unit 110 through mechanical connection units 111 and 121. When the atomizing unit 120 and the electrical unit 110 are mechanically connected to each other, a load 121R (described later) in the atomizing unit 120 is electrically connected to a power supply 10 provided in the electrical unit 110 through electrical connection terminals 110*t* and 120*t*. That is, the electrical connection terminals 110*t* and 120*t* form a connection unit capable of electrically disconnecting and connecting the load 121R from/to the power supply 10.

The atomizing unit 120 includes an inhalation component source to be inhaled by a user, and the load 121R configured to vaporize or atomize the inhalation component source with electric power from the power supply 10. The inhalation component source may include an aerosol source that generates aerosol and/or a flavor source that generates a flavor component.

The load 121R may be any element capable of generating aerosol and/or a flavor component from an aerosol source and/or a flavor source by receiving the electric power. The load 121R may be, for example, a heat generating element such as a heater or an element such as an ultrasound generator. Examples of the heat generating element include a heat generation resistor, a ceramic heater, and an induction heating type heater.

Hereinafter, a more detailed example of the atomizing unit 120 will be described with reference to FIG. 1 and FIG. 2. The atomizing unit 120 may include a reservoir 121P, a wick 121Q, and the load 121R. The reservoir 121P may be configured to store a liquid aerosol source or flavor source. The reservoir 121P may be, for example, a porous body made of a material such as a resin web. The wick 121Q may be a liquid holding member that draws the aerosol source or the flavor source from the reservoir 121P using capillary action. The wick 121Q may be made of, for example, glass fiber or porous ceramic.

The load 121R atomizes the aerosol source held by the wick 121Q or heats the flavor source held by the wick 121Q. The load 121R is formed of, for example, a resistive heating element (for example, a heating wire) wound around the wick 121Q.

The air that has flowed in from an inlet hole 122A passes through the vicinity of the load 121R in the atomizing unit 120. The inhalation component generated by the load 121R flows together with the air toward the inhalation port.

The aerosol source may be a liquid at ordinary temperature. For example, polyhydric alcohol may be used as the aerosol source. The aerosol source itself may contain the flavor component. Alternatively, the aerosol source may include a tobacco raw material that emits an inhaling flavor component by being heated or an extract deriving from the tobacco raw material.

Note that, although an example of the liquid aerosol source at ordinary temperature has been described in detail in the above-described embodiment, an aerosol source that is a solid at ordinary temperature may be also used instead of the liquid aerosol source.

The atomizing unit 120 may include a replaceable flavor unit 130. The flavor unit 130 includes a cylindrical body 131 that accommodates the flavor source. The cylindrical body 131 may include a membrane member 133 and a filter 132. The flavor source may be provided in a space formed by the membrane member 133 and the filter 132.

The atomizing unit 120 may include a breaking unit 90. The breaking unit 90 is a member for breaking a part of the membrane member 133 of the flavor unit 130. The breaking unit 90 may be held by a partition wall member 126 for partitioning into the atomizing unit 120 and the flavor unit 130. The partition wall member 126 is made of, for example, a polyacetal resin. The breaking unit 90 is, for example, a cylindrical hollow needle. An airflow path that pneumatically communicates between the atomizing unit 120 and the flavor unit 130 is formed by puncturing the membrane member 133 with a tip of the hollow needle. Here, it is preferable that an inside of the hollow needle is provided with a mesh having a roughness of not allowing the flavor source to pass through.

According to an example of the preferred embodiment, the flavor source in the flavor unit 130 imparts the inhaling flavor component to the aerosol generated by the load 121R of the atomizing unit 120. The flavor imparted to the aerosol by the flavor source is sent to the inhalation port of the inhalation component generation device 100. Thus, the inhalation component generation device 100 may have a plurality of inhalation component sources. Alternatively, the inhalation component generation device 100 may have only one inhalation component source.

The flavor source in the flavor unit 130 may be a solid at ordinary temperature. By way of example, the flavor source comprises an ingredient piece of a plant material which imparts the inhaling flavor component to the aerosol. Shredded tobacco or a forming body obtained by forming a tobacco material such as a tobacco raw material in a granular form, may be used as an ingredient piece which is a component of the flavor source. Alternatively, the flavor source may comprise a forming body obtained by forming a tobacco material into a sheet form. Also, the ingredient piece, which is a component of the flavor source, may comprise a plant (for example, mint, a herb, and the like) other than tobacco. The flavor source may be provided with flavor such as menthol.

The inhalation component generation device 100 may include a mouthpiece 142 having the inhalation port 141 through which a user inhales the inhalation component. The mouthpiece 142 may be configured to be detachably attached to the atomizing unit 120 or the flavor unit 130, or may be configured to be an integral part of the atomizing unit 120 or the flavor unit 130.

The electrical unit 110 may include the power supply 10, an inhalation sensor 20, a push button 30, a notification unit 40, and a control unit 50. The power supply 10 stores the electric power necessary for the operation of the flavor inhaler 100. The power supply 10 may be detachably attached to the electrical unit 110. The power supply 10 may be, for example, a rechargeable battery such as a lithium ion secondary battery.

When the atomizing unit 120 is connected to the electrical unit 110, the load 121R provided in the atomizing unit 120 is electrically connected to the power supply 10 of the electrical unit 110 (see FIG. 5).

The inhalation component generation device 100 may include a switch 140 capable of electrically connecting and disconnecting the load 121R to or from the power supply 10. The switch 140 is opened or closed by the control unit 50. The switch 140 may be comprised of, for example, a MOSFET.

When the switch 140 is turned on, the electric power is supplied from the power supply 10 to the load 121R. On the other hand, when the switch 140 is turned off, the supply of electric power from the power supply 10 to the load 121R is stopped. The turning on and off of the switch 140 is controlled by the control unit 50.

The control unit 50 may include an operation request sensor configured to detect an operation relating to an operation request of a user. The operation request sensor may be, for example, the push button 30 to be pressed by a user or the inhalation sensor 20 configured to detect a user's inhaling operation. The control unit 50 acquires an operation request signal to the load 121R and generates a command for operating the load 121R. In a specific example, the control unit 50 outputs the command for operating the load 121R to the switch 140, and the switch 140 is turned on according to this command. Thus, the control unit 50 is configured to control the supply of electric power from the power supply 10 to the load 121R. When the electric power is supplied from the power supply 10 to the load 121R, the inhalation component source is vaporized or atomized by the load 121R.

In addition, the inhalation component generation device 100 may include at least one of a voltage sensor 150, a current sensor 152, and a temperature sensor 154, where appropriate. Note that for convenience, no temperature sensor 154 is illustrated in FIG. 5 and FIG. 6.

The voltage sensor 150 may be configured to be capable of detecting a voltage of the power supply 10. The current sensor 152 may be configured to be capable of detecting an amount of current that has flowed out from the power supply 10 and an amount of current that has flowed into the power supply 10. The temperature sensor 154 may be configured to be capable of detecting a temperature in the vicinity of the power supply 10, for example. The control unit 50 is configured to be capable of acquiring outputs of the current sensor 152 and the temperature sensor 154. The control unit 50 performs various types of control using these outputs.

The inhalation sensor 20 may be a sensor that outputs a value (for example, a voltage value or a current value) that changes according to the flow rate of air (i.e., a user's puff operation) inhaled from the non-inhalation port side toward the inhalation port side. Examples of such a sensor include a condenser microphone sensor, and a known flow sensor.

FIG. 3 illustrates a specific example of the inhalation sensor 20. The inhalation sensor 20 illustrated in FIG. 3 includes a sensor body 21, a cover 22, and a substrate 23. The sensor body 21 is comprised of, for example, a capacitor. An electric capacity of the sensor body 21 changes due to vibration (pressure) generated by air inhaled from an air introduction hole 125 (i.e., air inhaled from the non-inhalation port side toward the inhalation port side). The cover 22 is provided on the inhalation port side with respect to the sensor body 21, and has an opening 22A. Providing the cover 22 having the opening 22A allows the electric capacity of the sensor body 21 to be changed easily, and improves the response characteristic of the sensor body 21. The substrate 23 outputs a value (here, a voltage value) indicating the electric capacity of the sensor body 21 (capacitor).

The inhalation component generation device 100, more specifically, the electrical unit 110 may be configured to be connectable to the charger 200 for charging the power supply 10 in the electrical unit 110 (see FIG. 6). When the charger 200 is connected to the electrical unit 110, the charger 200 is electrically connected to the power supply 10 of the electrical unit 110.

The electrical unit 110 may include a determination unit configured to determine whether the charger 200 is connected. The determination unit may be, for example, means for determining the presence or absence of connection of the charger 200 based on a change in potential difference between a pair of electrical terminals to which the charger 200 is connected. The determination unit is not limited to this means, and may be any means that can determine the presence or absence of the connection of the charger 200.

The charger 200 includes an external power supply 210 for charging the power supply 10 in the electrical unit 110. The inhalation component generation device 100 may be communicable with a processor 250 of the charger 200. The processor 250 may be configured to be capable of controlling at least one of the discharge from the power supply 10 to the external power supply 210 and the charge from the external power supply 210 to the power supply 10. In addition, the charger 200 may include a current sensor 230 configured to acquire a value of a charging current and a voltage sensor 240 configured to acquire a value of a charging voltage.

The control unit 50 may include a counter 52 configured to count the number of detecting the user's puff operations. In addition, the control unit 50 may include a timer 54 configured to detect the user's puff operation, that is, measure the time elapsed since acquisition of the operation request signal to the load 121R.

The notification unit 40 performs notification for notifying a user of various types of information. The notification unit 40 may be, for example, a light emitting element such as an LED. Instead of this, the notification unit 40 may be an element that generates sound, or a vibrator. The control unit 50 may be configured to be cable of controlling the notification unit 40 to operate in any one of a normal use mode, a charge request mode and an abnormality notification mode. The normal use mode, the charge request mode, and the abnormality notification mode will be described later.

When the notification unit 40 includes a light emitting element, it is preferable that the light emitting element is provided on a side surface 124 extending between the inhalation port end E1 and the non-inhalation port end E2 (see FIG. 1). In this case, a length from the inhalation port end E1 to the light emitting element is preferably 58 mm or more, more preferably 100 mm or more. Furthermore, it is preferable that a length from one end E1 to the other end E2 is 135 mm or less.

In addition, the light emitting element may be provided between the non-inhalation port end E2 of the inhalation component generation device 100 and one portion of the side surface 124 extending between the inhalation port end E1 and the non-inhalation port end E2. In this case, the length from one end E1 to the other end E2, i.e., the length from the inhalation port end E1 to the light emitting element is preferably 58 mm or more, more preferably 100 mm or more. Furthermore, it is preferable that the length from one end E1 to the other end E2 is 135 mm or less. This length may be set from the viewpoint of imitating the shape of the widely distributed cigarette and from the viewpoint that the notification unit 40 is within the field of view of a user when the user holds the end E1 in the user's mouth.

In this way, when the user uses the inhalation component generation device 100 by holding the inhalation end E1, the distance from the user's eyes to the other end E2 of the inhalation component generation device 100, i.e., to the light emitting element can be secured. Assuming that a distance between both eyes of a general user is 100 mm and considering the idea of the peripheral vision, when the light emitting element emits light in violet, the length from the inhalation port end E1 to the light emitting element is 58 mm or more and therefore the user can start to recognize the color of the light emitting element even in a state in which the user's line of sight is directed toward the front center. That is, the user can easily recognize the difference in color of the light emitting element even without staring the light emitting element. In addition, when the length from the inhalation port end E1 to the light emitting element is 100 mm or more, the user's recognition rate for violet exceeds 50%. Note that color recognition refers to the ability to distinguish between a specific color and the other color. Furthermore, it is not absolutely necessary to be able to distinguish between a plurality of colors belonging to similar colors, and it is only required to distinguish at least a plurality of colors from one another, the plurality of colors not belonging to similar colors and being easily distinguished from one another.

By the way, it should be noted that the length when the above-described user starts to recognize the color of the light emitting element and the length when the user's recognition rate for the color exceeds 50% are values in an example in which the light emitting element emits light in violet. In other words, the length from the inhalation port end E1 to the light emitting element may be determined based on the color that the user particularly wants to recognize among the light emission colors of the light emitting element.

In addition, when the light emitting element is provided on a part of the side surface 124 extending between the inhalation port end E1 and the non-inhalation port end E2, there is an advantage that the user can easily recognize the color of the light emitting element while holding the inhalation component generation device in the mouth.

Figure 7:
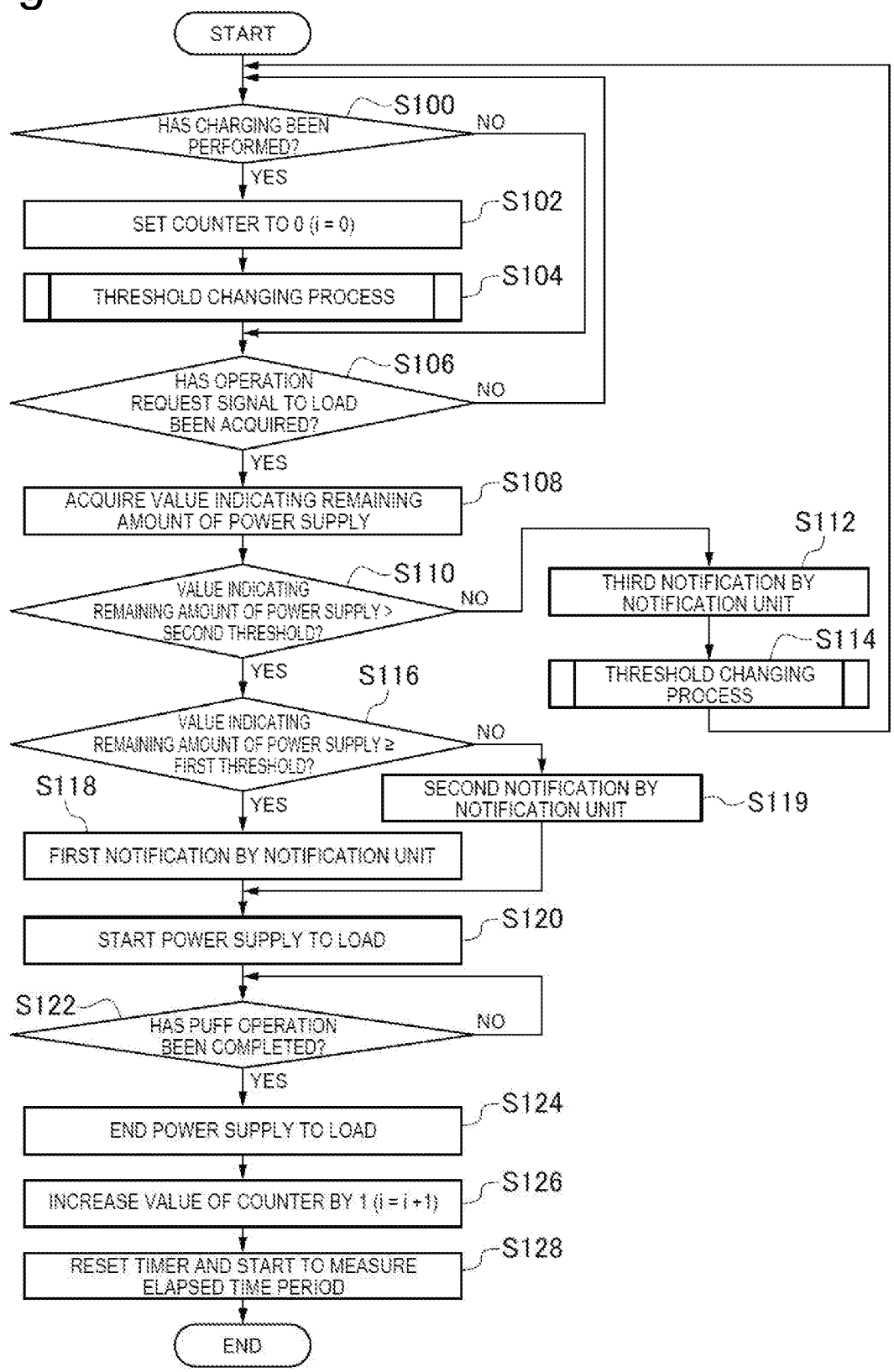
FIG. 7 is a flowchart illustrating an example of a control method of the inhalation component generation device.
Figure 8:
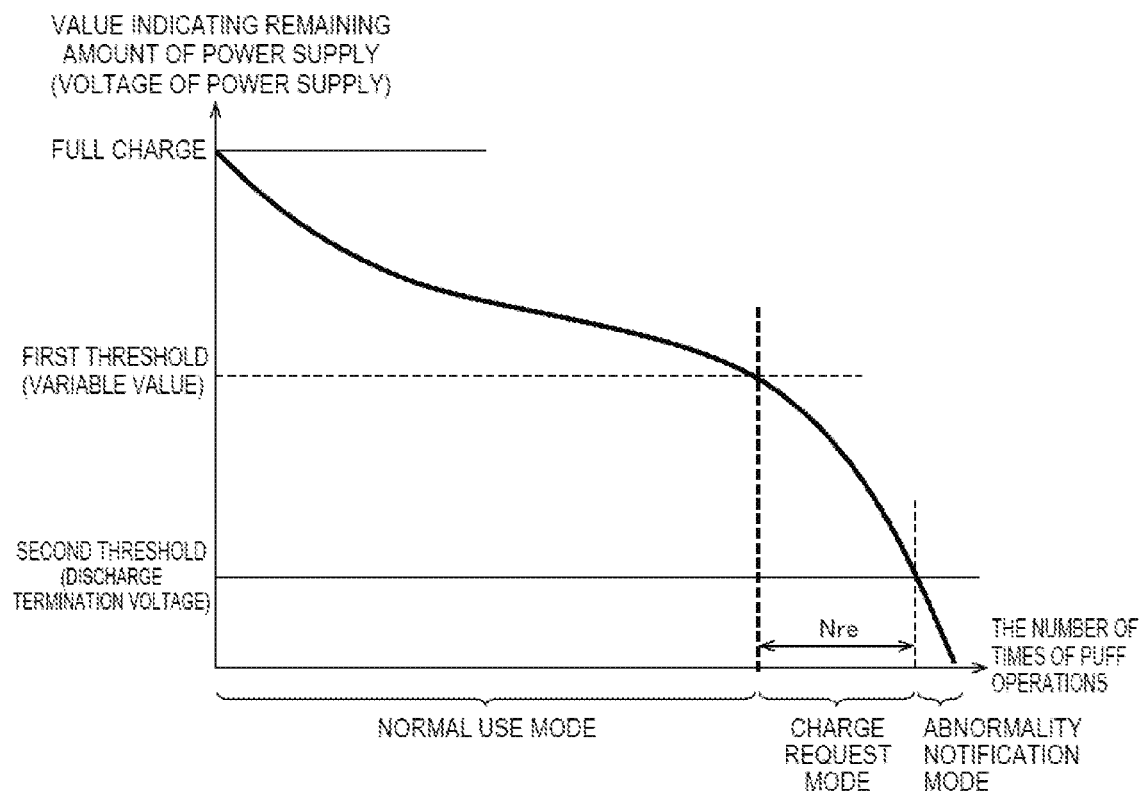
FIG. 8 is a graph showing a relationship between the number of times of puff operations by a user and a value indicating a remaining amount of a power supply.

FIG. 7 is a flowchart illustrating an example of a control method of the inhalation component generation device according to one embodiment. FIG. 8 shows a relationship between the number of times of puff operations by the user and a value indicating the remaining amount of the power supply.

During the following series of processing, it is preferable that the counter 52 measures the number of times that the user has performed a puff operation.

The control unit 50 monitors whether charging of the power supply 10 has been performed by the charger 200 (step S100). The determination as to whether charging has been performed can be made by monitoring a value indicating the remaining amount of the power supply 10. For example, when the value indicating the remaining amount of the power supply 10 has increased to a predetermined amount or more, the control unit 50 can determine that charging has been performed. Alternatively, when the current sensor 152 provided in the electrical unit 110 detects a charging current for charging the power supply 10, the control unit 50 may determine that charging has been performed. Alternatively, when communication means (not illustrated) capable of communicating between the electrical unit 110 and the charger 200 communicates that charging is being performed from the charger 200 to the electrical unit 110, the control unit 50 may determine that charging has been performed. Alternatively, when a signal requesting charging is transmitted from the electrical unit 110 to charger 200, the control unit 50 may determine that charging has been performed. Note that the communication between the electrical unit 110 and the charger 200 may be performed by power line communication (PLC) via a circuit without use of dedicated communication means.

The value indicating the remaining amount of the power supply 10 may be, for example, the voltage of the power supply 10, the state of charge (SOC) of the power supply 10 or the remaining capacity of the power supply. The voltage of the power supply 10 may be an open circuit voltage (OCV) acquired in a state in which the load 121R is not electrically connected to the power supply 10 or may be a closed circuit voltage (CCV) acquired in a state in which the load is electrically connected to the power supply. However, from the viewpoint of the accuracy of estimation of the remaining amount of the power supply 10, it is preferable that the value indicating the remaining amount of the power supply 10 is defined by the open circuit voltage (OCV) rather than by the closed circuit voltage (CCV) to eliminate the influences of changes in internal resistance and temperature due to voltage drop and discharge accompanying electrical connection of the load 121R.

When the charging has been performed, it is preferable that the control unit 50 sets a value of the counter 52 to "0" (step S102). As a result, the counter 52 can measure the number of times of puff operations from the charging start to the present.

In addition, the control unit 50 may perform a threshold changing process S104 as necessary when the charging is performed. The threshold changing process S104 will be described in detail below.

Furthermore, the control unit 50 waits until acquiring an operation request signal to the load 121R (step S106). The operation request signal to the load 121R is input to the control unit 50 from the above-described operation request sensor according to the operation of the user.

When acquiring the operation request signal to the load 121R, the control unit 50 acquires a value indicating the remaining amount of the power supply 10 (step S108). An example of the value indicating the remaining amount of the power supply 10 is as described above. The acquired value indicating the remaining amount of the power supply 10 is stored in a memory 58.

When the acquired value indicating the remaining amount of the power supply 10 is less than the second threshold, the control unit 50 controls the notification unit 40 in the abnormality notification mode to cause the notification unit 40 to perform the third notification (steps S110 and S112). The abnormality notification mode is a mode indicating that the remaining amount of the power supply 10 is zero or extremely low, and therefore the load 121R cannot normally generate the inhalation component from the inhalation component source.

The second threshold may be defined by, for example, a value corresponding to the remaining amount of the power supply that is zero or in the vicinity of zero. When the value indicating the remaining amount of the power supply 10 is the voltage of the power supply 10, the second threshold may be defined by, for example, a discharge termination voltage or a voltage slightly higher than the discharge termination voltage. When the value indicating the remaining amount of the power supply 10 is the state of charge or remaining capacity of the power supply 10, the second threshold may be defined by, for example, the state of charge or remaining capacity corresponding to the discharge termination voltage or the voltage slightly higher than the discharge termination voltage.

The control unit 50 may wait in the abnormality notification mode without supplying the electric power to the load 121R. Alternatively, the control unit 50 may automatically turn off the inhalation component generation device 100 when entering the abnormality notification mode.

Preferably, when entering the abnormality notification mode, the control unit 50 performs the threshold changing process (step S114) as necessary. Details of the threshold changing process S114 will be described later.

When the acquired value indicating the remaining amount of the power supply 10 is equal to or more than the first threshold which is larger than the second threshold, the control unit 50 controls the notification unit 40 in the normal use mode to cause the notification unit 40 to perform first notification (steps S110, S116, and S118). The normal use mode is a mode in which the remaining amount of the power supply 10 is sufficiently large and therefore the load 121R can generate a inhalation component from the inhalation component source. The first threshold is used to distinguish between the normal use mode and the charge request mode described later.

In the normal use mode, the control unit 50 acquires an operation request signal to the load 121R and generates a command for operating the load 121R. The switch 140 is turned on based on this command, whereby the electric power is supplied to the load 121R (step S120). Thereby, the load 121R generates an inhalation component from the inhalation component source. The generated inhalation component is inhaled by the user through the inhalation port. The control unit 50 may control the amount of electric power to be supplied to the load 121R by pulse width control (PWM).

When the control unit 50 determines that the operation request operation (inhaling operation) of the user has been completed based on the operation request signal from the operation request sensor, the control unit 50 turns off the switch 140 to stop the power supply to the load 121R (step S122, step S124). In addition, the control unit 50 may forcibly stop the power supply to the load 121R when the operation request operation (inhaling operation) of the user continues beyond the predetermined period. The above-described predetermined period for forcibly stopping the power supply to the load 121R may be set based on the period of one inhaling operation of a normal user, and, for example, may be set in the range of 2 to 4 seconds.

When the control unit 50 detects a puff operation of the user based on the operation request signal from the operation request sensor, the control unit 50 increases by one the value of the counter 52 that measures the number of times of puff operations. Furthermore, the control unit 50 resets the timer 54, and measures the elapsed time period by the timer 54 (step S128). As a result, the control unit 50 can use the timer 54 to measure the neglect time period which is a period during which the electric power is not supplied to the load 121R.

When the power supply to the load 121R is stopped, the control unit 50 returns to a standby state, and the control unit 50 monitors again whether the charging has been performed (step S100) and whether the operation request signal to the load 121R has been acquired (step S106).

When the value indicating the remaining amount of the power supply acquired in step S108 is less than the first threshold and equal to or more than the second threshold, the control unit 50 controls the notification unit 40 in the charge request mode and causes the notification unit 40 to perform the second notification (steps S110, S116 and S119). The charge request mode is provided for notifying the user of a decrease in the remaining amount of the power supply 10 and requesting the user to charge although the inhalation component can be generated by the power supply to the load 121R.

Also in the charge request mode, the control unit 50 acquires an operation request signal to the load 121R and generates a command for operating the load 121R, as in the normal use mode. The switch 140 is turned on based on this command, whereby the electric power is supplied to the load 121R (step S120). Thereby, the load 121R generates an inhalation component from the inhalation component source. The steps (steps S120, S122, and S124) from the start to the end of the power supply to the load 121R in the charge request mode can be performed as in the normal use mode, as described above. Furthermore, when the control unit 50 detects a user's puff operation, the control unit 50 also increases the value of the counter 52 by one even in the charge request mode (step S126). Furthermore, the control unit 50 resets the timer 54, and measures the elapsed time period by the timer 54 (step S128). As a result, the control unit 50 can use the timer 54 to measure the neglect time period which is a period during which the electric power is not supplied to the load 121R.

The above-described first threshold is a variable value that can be changed based on the operation request signal to the load 121R, the operation request signal being acquired by the control unit 50. That is, the conditions for switching between the normal use mode and the charge request mode are changed based on the operation request signal. The first threshold is automatically changed by the control unit 50, for example, in the above-described threshold changing process. Preferably, the first threshold is changed based on a value related to the power supply from the power supply 10 to the load 121R. This value related to the power supply may be the voltage of the power supply 10, the state of charge of the power supply 10, or the remaining capacity of the power supply. More specifically, the first threshold is changed based on, for example, the voltage drop of the power supply 10 for each puff, the decrease in the state of charge of the power supply 10 for each puff, or the decrease amount in the remaining capacity of the power supply 10 for each puff.

Here, a curve representing the relationship between the value indicating the remaining amount of the power supply and the number of times of puff operations shown in FIG. 8 changes according to the puff operation conditions (inhalation time period and inhalation amount), the degree of degradation of the power supply 10 and the like.

The operation request signal is a signal output according to a way of use by the user. For example, the inhalation sensor 20 outputs an output signal (operation request signal) according to the inhalation amount per one puff operation of the user and the inhalation time period per one puff operation of the user (see the upper graphs in FIG. 9 and FIG. 10).

Therefore, when the first threshold can be changed based on an operation request signal to the load 121R, for example, a value related to the power supply to the load 121R, the first threshold can be changed according to the way of use of the load 121R. Thereby, the timing to perform the second notification can be changed according to the way of use of the inhalation component generation device by the user. Therefore, according to this aspect, it is possible to perform the second notification at a more appropriate timing according to the way of use of the inhalation component generation device by the user.

(Mode of Notification by Notification Unit)

The first notification, the second notification, and the third notification described above are different from one another. That is, in the above-described embodiment, the notification to be performed by the notification unit 40 is different among the normal use mode, the charge request mode, and the abnormality notification mode. Therefore, the notification unit 40 can cause the user to recognize the remaining amount of the power supply 10 and/or the distinction among the modes by issuing at least three different types of notification according to the remaining amount of the power supply 10.

Thereby, the notification unit 40 can notify the user of the difference among the normal use mode, the charge request mode, and the abnormality notification mode by different types of notification. An inhalation component generation device such as an electronic cigarette must include, as essential components, a reservoir 121P and a flavor unit 130 for storing or accommodating an aerosol source or/and a flavor source, and a component such as the power supply 10 that is difficult to be miniaturized, as well as imitate the shape and weight of widely distributed cigarettes. Therefore, constraints on user interface (U/I) and layout (L/O) are particularly severe. In such an inhalation component generation device, the notification unit 40 can cause the user to effectively recognize the difference among the normal use mode, the charge request mode, and the abnormality notification mode using the different types of notification, for example, the difference in the mode of the notification.

Furthermore, the notification unit 40 can provide the notification for requesting charging of the power supply 10 to the user before the remaining amount of the power supply 10 is depleted, by notifying the user that the remaining amount of the power supply 10 is reduced, by issuing the second notification before the third notification. Here, it is known that deterioration of the power supply 10 is promoted when the remaining amount of the power supply 10 is depleted. According to this aspect, the promotion of the deterioration of the power supply 10 can be suppressed by encouraging the charging of the power supply 10 before the remaining amount of the power supply 10 is depleted.

It is preferable that the notification unit 40 includes a light emitting element. In this case, the first notification, the second notification, and the third notification may be configured by a first light emission color, a second light emission color, and a third light emission color, respectively, to be emitted by the light emitting element. Here, the first light emission color, the second light emission color, and the third light emission color are different from one another.

More preferably, the first light emission color includes a cold color, the second light emission color includes an intermediate color, and the third light emission color includes a warm color. Here, the "intermediate color" as the second light emission color is defined by the color positioned between the first light emission color that is a "cold color" and the third light emission color that is a "warm color" in the hue circle.

The "hue circle" is defined by, for example, a hue circle in which hues in the Munsell color system are annularly arranged in an order. The "warm color" may be defined by light having a light spectrum peak in a region having hues of 10RP to 10Y in the Munsell color system or in a wavelength band of 570 nm to 830 nm. Examples of the "warm color" may include red. The "cold color" may be defined by light having a light spectrum peak in a region having hues of 5BG to 5PB in the Munsell color system or in a wavelength band of 450 nm to 500 nm. Examples of the "cold color" may include blue. The "intermediate color" may be defined by light having a light spectrum peak in a region having hues of 5PB to 10RP in the Munsell color system or in a wavelength band of 380 nm to 450 nm. Examples of the "intermediate color" may include violet.

Since the third light emission color in the abnormality notification mode includes a warm color, it is possible to effectively impress the user that an abnormality has occurred, specifically, that the remaining amount of the power supply 10 is depleted. On the other hand, since the first light emission color in the normal use mode includes a cold color, it is possible to impress the user that the inhalation component generation device 100 is operating without any problem. Furthermore, since the second light emission color in the charge request mode is an intermediate color between the first light emission color and the third light emission color, it is possible to effectively impress the user that the normal use mode in which the remaining amount of the power supply 10 is sufficient is being shifted to the abnormal notification mode in which the remaining amount of the power supply 10 is depleted.

Preferably, the distance on the hue circle between a complementary color of the first light emission color and the third light emission color is shorter than the distance on the hue circle between the complementary color of the first light emission color and the second light emission color. Alternatively or in addition to this, it is preferable that the distance on the hue circle between a complementary color of the third light emission color and the first light emission color is shorter than the distance on the hue circle between the complementary color of the third light emission color and the second light emission color.

Here, the "complementary color" of a certain color means a color positioned on the hue circle in the opposite (in other words, diagonally opposite) to the color. The combination of a certain color and its complementary color corresponds to a combination of colors that stand out from each other. Therefore, when the third light emission color is closer to the complementary color of the first light emission color on the hue circle than the second light emission color, the user can more easily distinguish the third light emission color from the first light emission color. Thereby, it is possible to effectively impress the user that the mode relating to the third light emission color is a mode antithetical to the normal use mode relating to the first light emission color, that is, the abnormality notification mode.

The wavelength of the light corresponding to the second light emission color may be closer to the wavelength of the light corresponding to the first light emission color than the wavelength of the light corresponding to the third light emission color. In particular, when the light emitting element has a light spectrum peak that protrudes in a specific wavelength band as in, for example, an LED, it is preferable that the wavelength of light in each light emission color satisfies such a relationship.

As an example of a preferred embodiment, the first notification may be configured by blue light to be emitted by the light emitting element, the second notification may be configured by violet light to be emitted by the light emitting element, and the third notification may be configured by red light to be emitted by the light emitting element.

Figure 9:
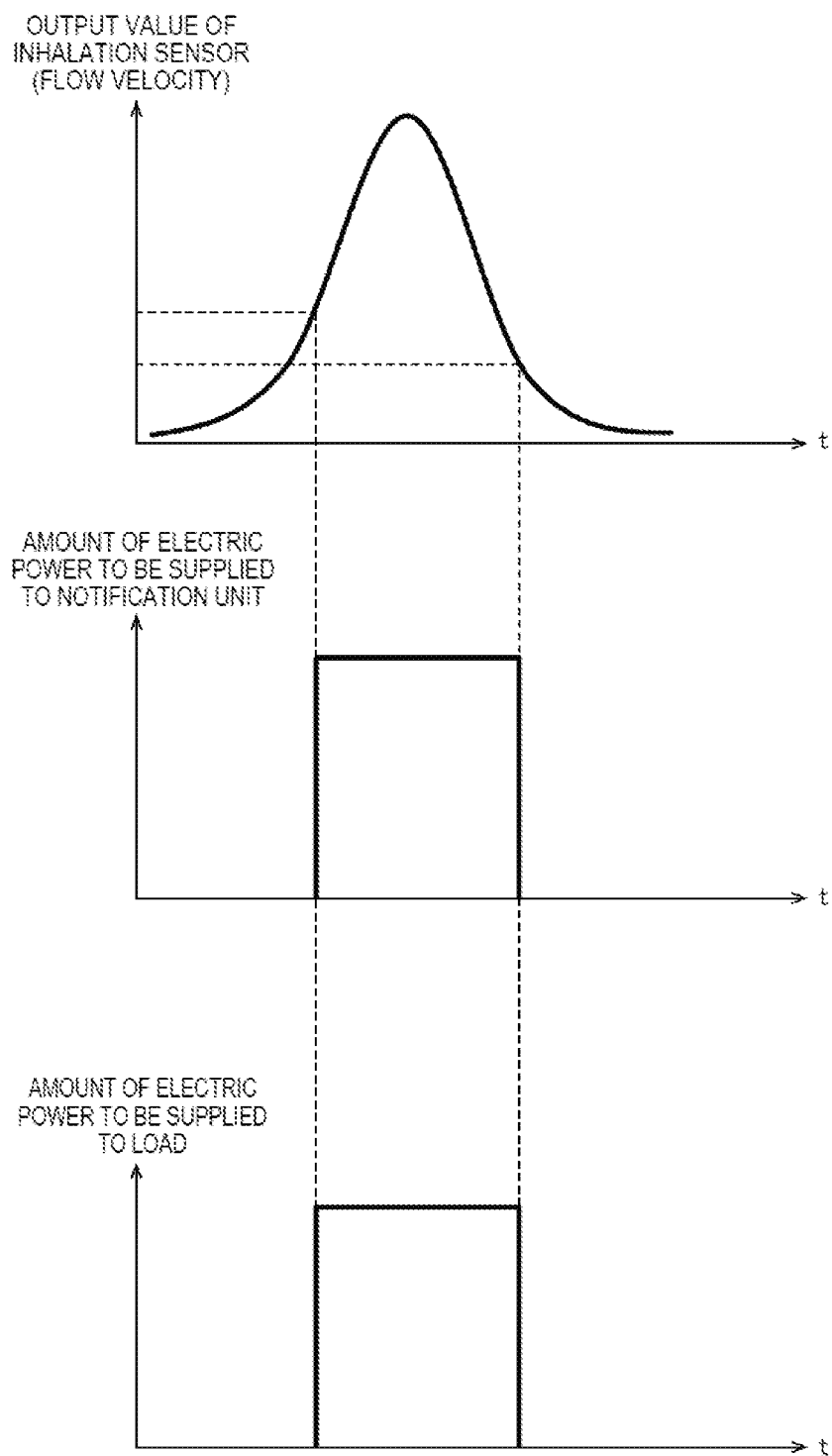
FIG. 9 is a graph showing an example of a light emission pattern of a light emitting element in the normal use mode and the charge request mode
Figure 10:
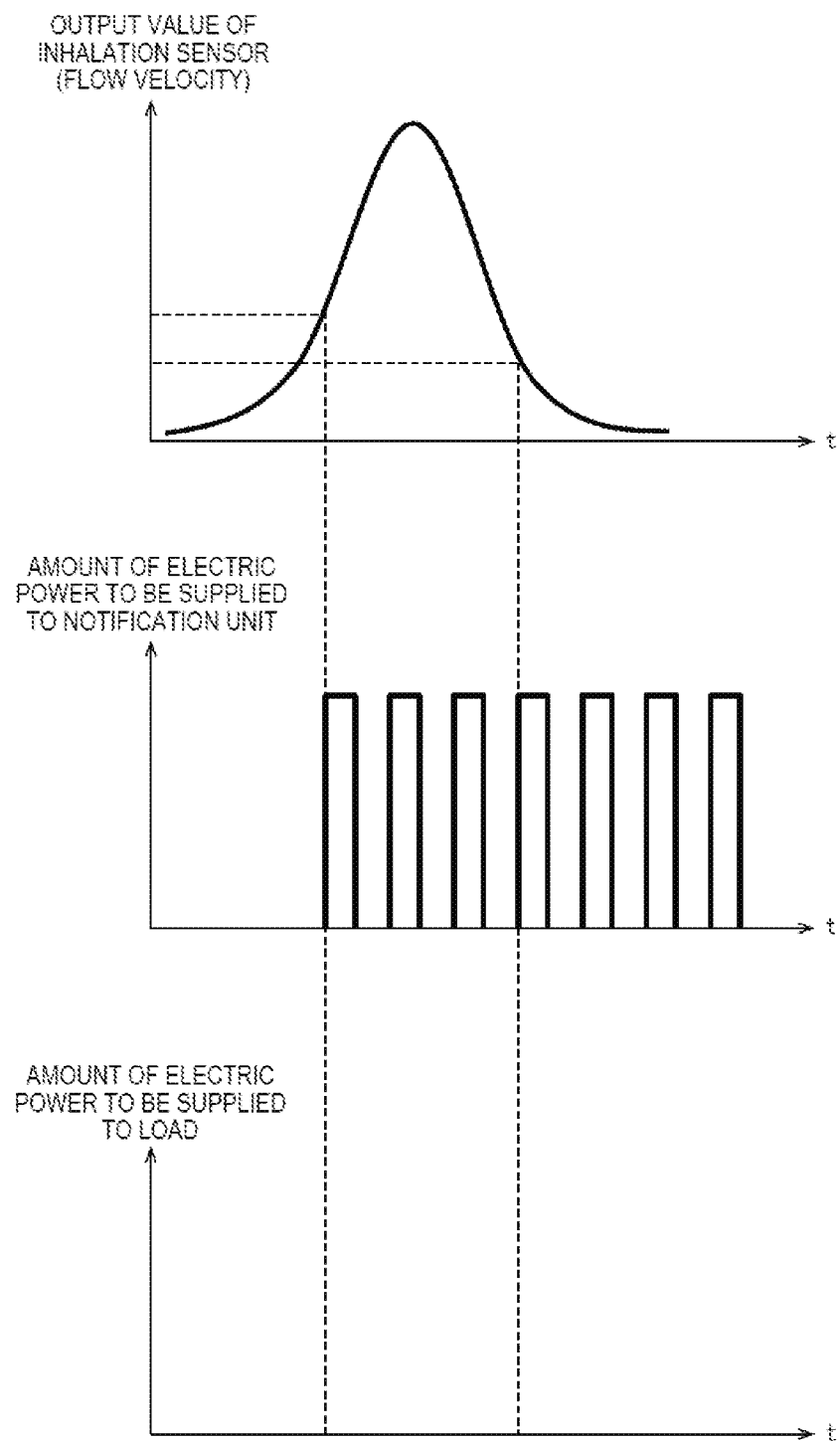
FIG. 10 is a graph showing an example of a light emission pattern of the light emitting element in the abnormality notification mode.

Next, with reference to FIG. 9 and FIG. 10, an example of a light emission pattern of the light emitting element will be described. FIG. 9 is a graph showing an example of a light emission pattern of the light emitting element in the normal use mode and the charge request mode. FIG. 10 is a diagram showing an example of the light emission pattern of the light emitting element in the abnormality notification mode. In each of FIGS. 9 and 10, the upper graph shows the time dependency of the output value of the operation request sensor, for example, the inhalation sensor 20. In each of FIG. 9 and FIG. 10, the middle graph shows the time dependency of the power supply to the light emitting element. In each of FIG. 9 and FIG. 10, the lower graph shows the time dependency of the power supply to the load 121R.

The light emitting element may continuously emit light in each of the normal use mode, the charge request mode, and the abnormality notification mode, or may blink by repeating light emission and non-light emission. In the illustrated example, the light emitting element emits light for a desired period in the normal use mode and the charge request mode. On the other hand, the light emitting element repeats light emission and non-light emission in the abnormality notification mode.

In each of the normal use mode, the charge request mode, and the abnormality notification mode, the control unit 50 may start to emit light from the light emitting element using the operation request signal as a trigger. For example, in the case where the operation request sensor is the inhalation sensor 20 that outputs a value related to the flow velocity in the inhalation component generation device 100, as shown in FIG. 9 and FIG. 10, when the output value of the inhalation sensor 20 exceeds a predetermined threshold value. the control unit 50 may start to supply the electric power to the light emitting element to cause the light emitting element to emit light.

Furthermore, in the normal use mode and the charge request mode, when the control unit 50 determines that the operation request operation (inhaling operation) of the user is completed, the control unit 50 may end the light emission of the light emitting element. For example, in the case where the operation request sensor is the inhalation sensor 20 that outputs a value related to the flow velocity in the inhalation component generation device 100, as shown in FIG. 9, when the output value of the inhalation sensor 20 falls below another predetermined threshold, the control unit 50 may stop the supply of electric power to the light emitting element to cause the light emitting element to emit no light. That is, the control unit 50 variably controls the periods of the first notification and the second notification performed by the notification unit 40 according to the period in which the operation request signal from the inhalation sensor 20 is continuously acquired. Although the method of controlling the notification unit 40 based on the operation request signal from the inhalation sensor 20 has been described here, the operation request signal may be output from a sensor other than the inhalation sensor 20. For example, when the push button 30 is used, the control unit 50 may variably control the periods of the first notification and the second notification performed by the notification unit 40 according to the period in which the operation request signal from the push button 30 is continuously acquired.

It is preferable that the light emission patterns of the light emitting element in the first notification in the normal use mode and in the second notification in the charge request mode are the same (see FIG. 9). Specifically, at least one, and more preferably both of the notification timings and notification periods of the first notification and the second notification when the control unit 50 has detected the operation request signal may be the same as each other. Setting the notification pattern (light emission pattern) for the first notification to be the same as that for the second notification while setting the light emission color in the second notification to be different from that in the first notification, in the second notification, i.e., in the charge request mode enables the user to easily recognize that the inhalation component can be generated from the inhalation component source, as in the first notification, i.e., the normal use mode.

Furthermore, as shown in FIG. 9, the timings at which the notification unit 40 starts and ends the first notification and the second notification may be the same as the timing at which the supply of electric power to the load 121R is started and the timing at which the supply is ended, respectively.

Alternatively, the timing for ending the second notification in the charge request mode may be longer than the timing for ending the supply of electric power to the load 121R, more preferably the timing for ending the puff operation.

The control unit 50 may be configured to control the notification unit 40 to perform the third notification only during a predetermined period that does not depend on the period in which the operation request signal is continuously acquired (see FIG. 10). That is, the notification unit 40 may perform the third notification only for a predetermined period without being influenced by the time period of the user's puff operation. In this case, it is preferable that the period in which the notification unit 40 performs each of the first notification and the second notification is shorter than the above-described predetermined period in which the third notification is performed. For example, the predetermined period in which the third notification is performed may be set to be longer than the period of one inhaling operation of a normal user, and may be set in the range of 4.5 to 6 seconds, for example.

According to the above-described aspect, the third notification in the abnormality notification mode can be easily distinguished from the first notification in the normal use mode and the second notification in the charge request mode. In addition, since the third notification continues for a longer period than each of the first notification in the normal use mode and the second notification in the charge request mode, the user can be effectively notified that charging is required.

Note that in the present embodiment, the aspect in which the first notification in the normal use mode is configured by blue light to be performed by the light emitting element, the second notification in the charge request mode is configured by violet light to be performed by the light emitting element, and the third notification in the abnormality notification mode is configured by red light to be performed by the light emitting element has been described. Instead of this aspect, in each notification, the light emitting element may be configured by a plurality of light emitting colors. More specifically, the light emission color of the light emitting element may be changed even in the same mode according to the elapsed time period since the start of each notification. In addition, the light emitting element may emit light in a plurality of light emission colors at the same time.

That is, at least a part of the light emitting element may be configured by blue light in at least a partial period of the first notification in the normal use mode, at least a part of the light emitting element may be configured by violet light in at least a partial period of the second notification in the charge request mode, and at least a part of the light emitting element may be configured by red light in at least a partial period of the third notification in the abnormality notification mode.

(Threshold Changing Process)

Figure 11:
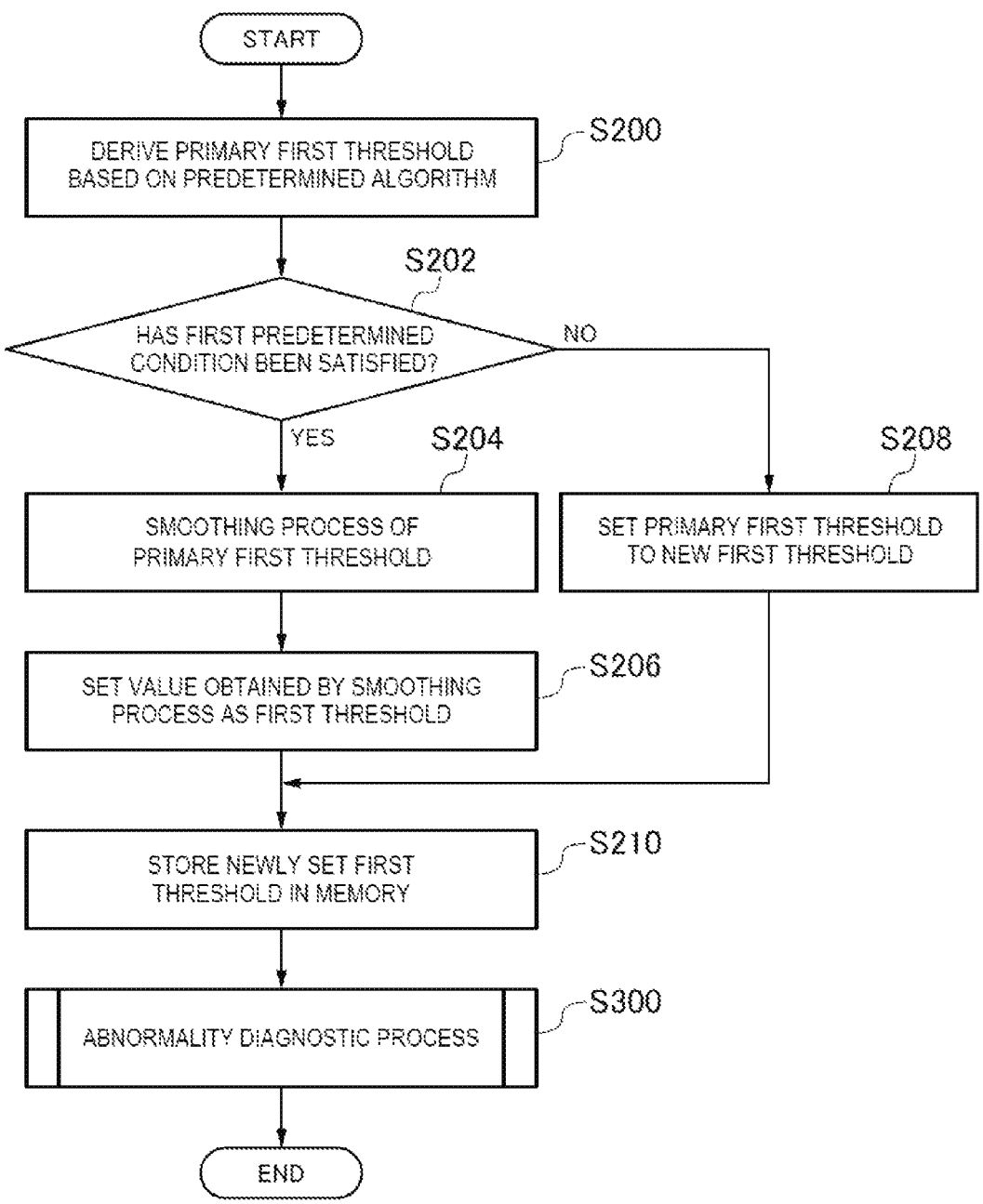
FIG. 11 is a flowchart illustrating an example of a threshold changing process.

The above-described threshold changing process will be described in detail. FIG. 11 illustrates an example of a flowchart of a threshold changing process. It is preferable that the control unit 50 performs the threshold changing process S114 when the value indicating the remaining amount of the power supply 10 becomes equal to or less than the second threshold.

Figure 12:
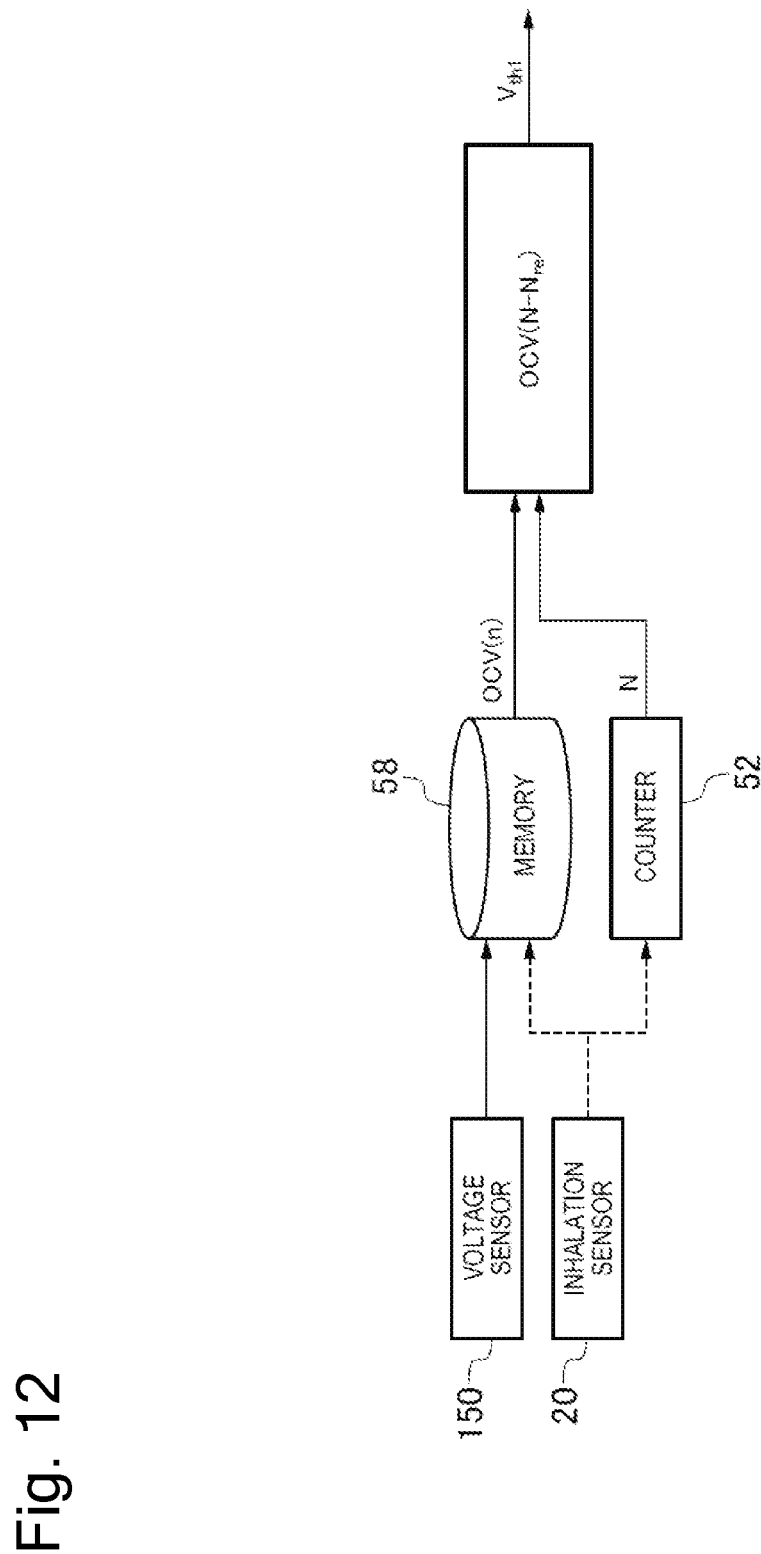
FIG. 12 illustrates an example of a block diagram of a control unit for performing a predetermined algorithm.

In the threshold changing process, a primary first threshold is derived based on a predetermined algorithm (step S200). FIG. 12 illustrates a block diagram of a control unit for performing the predetermined algorithm according to the present example.

In the example illustrated in FIG. 12, the value indicating the remaining amount of the power supply 10 is defined by the voltage of the power supply 10. In this case, the full charge may be defined by a fully charged voltage, and the second threshold may be defined by the discharge termination voltage. Furthermore, in this case, in the flowchart illustrated in FIG. 7, the control unit 50 acquires the voltage of the power supply 10 as a value indicating the remaining amount of the power supply 10. It is preferable that the voltage of the power supply 10 is an open circuit voltage (OCV) acquired in a state in which the switch 140 is turned off. The open circuit voltage (OCV) is stored in a memory 58 each time a puff operation is performed.

The predetermined algorithm according to the present example is performed when the voltage of the power supply 10 is equal to or lower than the discharge termination voltage. In this algorithm, the first threshold is changed based on the value of the voltage of the power supply 10 when the load 121R is operated a predetermined number of times before the voltage of the power supply 10 reaches the discharge termination voltage. Specifically, the control unit 50 acquires, from the memory 58, the voltage (OCV (N−$N_{re}$)) of the power supply 10 acquired a predetermined number of times ($N_{re}$) before the number of times (N) of puff operations measured after the start of charging, and sets the acquired voltage as the primary first threshold (see FIG. 12).

When a first predetermined condition is not satisfied, the control unit 50 sets the primary first threshold to a new first threshold (steps S202 and S208). When the first predetermined condition is satisfied, the control unit 50 sets, to the first threshold, a value obtained by performing the smoothing process on the primary first threshold (steps S202, S204, and S206). Here, the first predetermined condition may be, for example, a condition that the state of health of the power supply 10 has not progressed beyond a predetermined determination state, as described later. The smoothing process will be described later.

The predetermined number of times ($N_{re}$) may be a preset fixed value or a variable value that can be set by the user. As a specific example, the predetermined number of times ($N_{re}$) is, but not particularly limited to, preferably 15 to 35 times, more preferably 20 to 30 times.

It is preferable that the predetermined number of times ($N_{re}$) is smaller than the number of usable times of the unused inhalation component source. When the inhalation component generation device 100 has a plurality of inhalation component sources, it is more preferable that the predetermined number of times is smaller than the number of usable times from the smallest unused inhalation component source among the plurality of inhalation component sources. For example, when the inhalation component generation device 100 includes the atomizing unit 120 including an aerosol source and the flavor unit 130 including a flavor source, the predetermined number of times may be set to be smaller than a smaller value of the numbers of usable times of the atomizing unit 120 and the flavor unit 130.

Here, the number of usable times may be a value set in advance according to the design of the atomizing unit 120 or the flavor unit 130. The number of usable times may be, for example, the maximum number of uses when an inhaling smoke amount for each puff is within the design range in advance for each inhalation component source, and the maximum number of uses when the inhalation component for each puff is within the design range.

Setting the predetermined number of times ($N_{re}$) to be smaller than the number of usable times of the unused inhalation component source can prevent the atomizing unit 120 or the flavor unit 130 from reaching the replacement timing. Therefore, it is possible to suppress a situation in which the recognition that the puff operation can be performed about the predetermined number of times in the charge request mode is overturned.

It is preferable that the control unit 50 performs the smoothing process to make the primary first threshold derived by the predetermined algorithm close to at least one of the plurality of first thresholds that have been previously changed, as necessary (step S204). In this case, the control unit 50 sets a first threshold based on the value derived by performing the smoothing process (step S206).

Note that it is preferable that the first threshold is stored in the memory 58 each time it is changed (step S210). That is, the memory 58 stores the history of the first threshold. By the above-described threshold changing process, the value of the first threshold used in the flowchart illustrated in FIG. 7 is changed.

When the first threshold is changed, it is preferable to perform an abnormality diagnostic process S300, as necessary. The abnormality diagnostic process S300 will be described later.

By changing the first threshold by the threshold changing process according to the present example, it is possible to secure puff operations of about a predetermined number of times before shifting from the charge request mode to the abnormality notification mode. That is, the number of times of puff operations that can be performed in the charge request mode can be secured regardless of the puff operation conditions (pattern of the operation request signal) of the user and the degree of degradation of the power supply 10. This can prevent the inhalation component generation device 100 from suddenly becoming unusable after entering the charge request mode, and therefore there can be provided the inhalation component generation device 100 that is highly convenient for the user.

(Another Example of Predetermined Algorithm)

Figure 13:
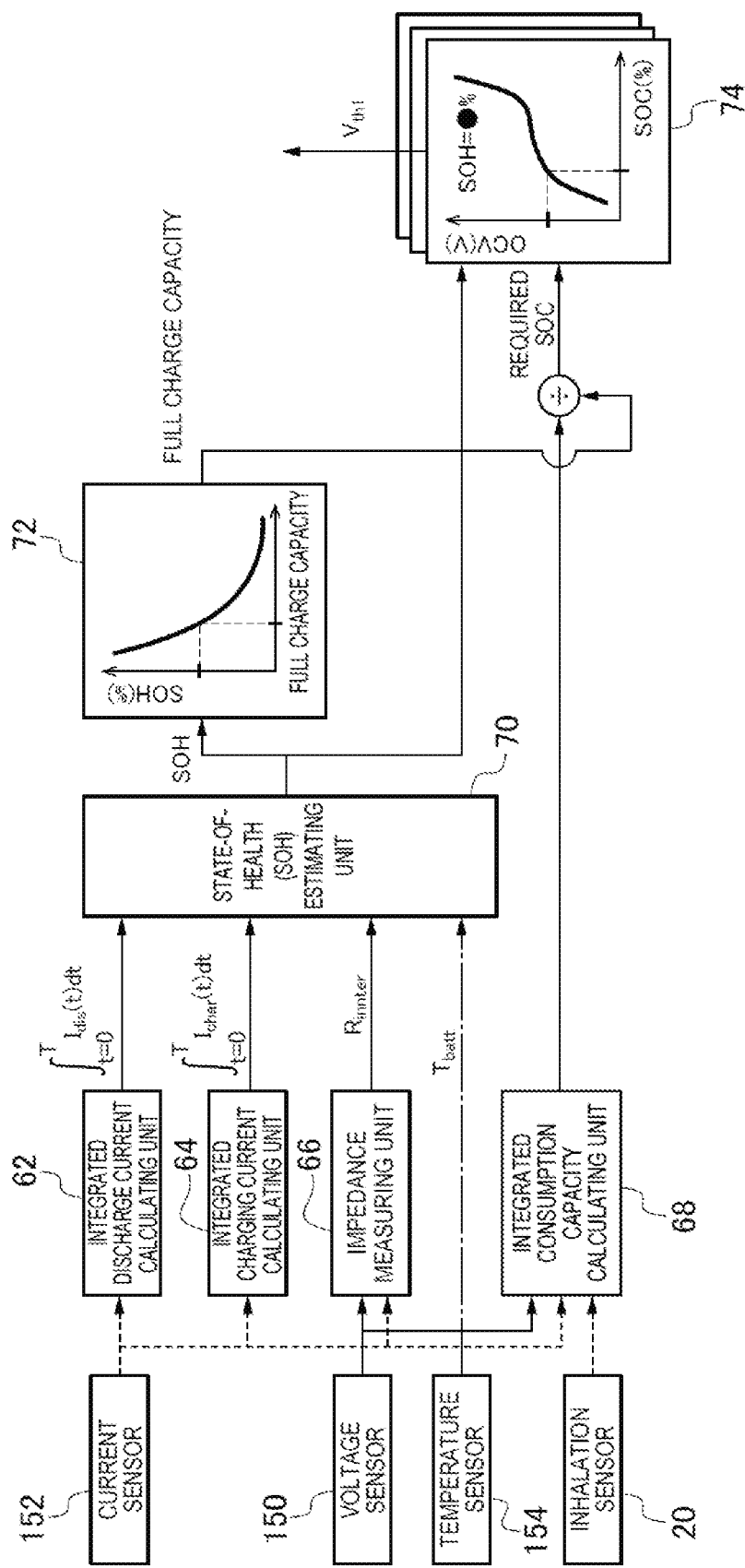
FIG. 13 illustrates another example of a block diagram for performing a predetermined algorithm.

Next, another example of a predetermined algorithm will be described. FIG. 13 illustrates a block diagram of a control unit for performing the predetermined algorithm according to the present example.

In the example illustrated in FIG. 13, the value indicating the remaining amount of the power supply 10 is defined by the state of charge (SOC) or remaining capacity of the power supply 10. In this case, the second threshold may be the state of charge or remaining capacity of the power supply when the voltage of the power supply reaches the discharge termination voltage. Furthermore, in this case, in the flowchart illustrated in FIG. 7, the control unit 50 acquires the state of charge or remaining capacity of the power supply 10 as a value indicating the remaining amount of the power supply 10. The acquired state of charge or remaining capacity is stored in the memory 58 each time a puff operation is performed. When the state of charge (SOC) of the power supply 10 is used as a value indicating the remaining amount of the power supply 10, the second threshold in step S110 and the first threshold in step S116 are values suitable for comparison with the state of charge (SOC), and the dimension (unit) is (%). On the other hand, when the remaining capacity of the power supply 10 is used as a value indicating the remaining amount of the power supply 10, the first threshold in step S110 and the second threshold in step S116 are values suitable for comparison with the remaining capacity, and the dimension (unit) is (Wh).

It is preferable that the predetermined algorithm according to the present example is performed when the state of charge of the power supply 10 becomes equal to or less than the state of charge corresponding to the discharge termination voltage. In this algorithm, the first threshold is changed based on a value obtained by adding, to the second threshold, the state of charge or remaining capacity of the power supply 10 required for operating the load 121R by an amount corresponding to the above-described predetermined number of times.

The state of charge (SOC) or remaining capacity of the power supply 10 can be estimated by, for example, a known SOC-OCV method, current integration method (coulomb counting method) or the like. FIG. 13 illustrates an example using the SOC-OCV method. In this method, the control unit 50 includes a state-of-health estimating unit 70 configured to estimate the state of health of the power supply 10. Furthermore, the control unit 50 includes an integrated discharge current calculating unit 62, an integrated charging current calculating unit 64, an impedance measuring unit 66, and an integrated consumption capacity calculating unit 68. The integrated discharge current calculating unit 62 and the integrated charging current calculating unit 64 calculate the integrated value of the current flowing out of the power supply 10 and the integrated value of the current flowing into the power supply 10, respectively, using the current sensor 152. The impedance measuring unit 66 measures the impedance (internal resistance) using the voltage sensor 150 and the current sensor 152. The state-of-health estimating unit 70 acquires the state of health (SOH) of the power supply 10 based on the integrated value of the current flowing out of the power supply 10, the integrated value of the current flowing into the power supply 10, the impedance, and the temperature measured using the temperature sensor 154 by a known method.

The control unit 50 acquires the full charging capacity of the power supply 10 based on the state of health (SOH) of the power supply 10 by the mapping 72. Using the integrated consumption capacity and full charging capacity of the power supply 10 derived by the integrated consumption capacity calculating unit 68, the state of charge or remaining capacity of the power supply 10 required for operating the load 121R by an amount corresponding to the above-described predetermined number of times is derived. The open circuit voltage ($V_{th1}$) is derived, as a primary first threshold, from the required state of charge or remaining capacity of the power supply 10 derived using the mapping 74 between the state of charge (SOC) of the power supply 10 and the open circuit voltage of the power supply 10.

Since it is known that the mapping 74 between the state of charge (SOC) of the power supply 10 and the open circuit voltage of the power supply 10 depends on the state of health of the power supply 10, it is preferable that multiple mappings 74 corresponding to the state of health of the power supply are stored in the memory 58 in advance.

As described above, in the SOC-OCV method, the state of charge can be estimated based on the voltage of the power supply acquired at the time of use using a fact that the state of charge and the voltage of the power supply have a one-to-one relationship and using the mapping between the state of charge and the voltage of the power supply according to the type of the power supply in advance. Here, it is preferable that the voltage of the power supply is an open circuit voltage.

In the present example, the algorithm for deriving the open circuit voltage as a primary first threshold has been described in detail. Instead of this, when the state of charge (SOC) or remaining capacity of the power supply 10 is used as a value indicating the remaining amount of the power supply 10, the "state of charge or remaining capacity of the power supply 10 required for operating the load 121R by an amount corresponding to the predetermined number of times" that is derived in the previous stage of the mapping 74 illustrated in in FIG. 13 may be used as a primary first threshold. Alternatively, instead of this, the "state of charge or remaining capacity of the power supply 10 required for operating the load 121R by an amount corresponding to the predetermined number of times" that is derived using the mapping 74 or/and the full charging capacity, and the open circuit voltage derived by the mapping 74 may be used as a primary first threshold.

Furthermore, in the present example, although the algorithm for deriving the primary first threshold is different from the example described above, the threshold changing process can be performed as in the flowchart illustrated in FIG. 11.

(Another Example of Threshold Changing Process)

Figure 14:
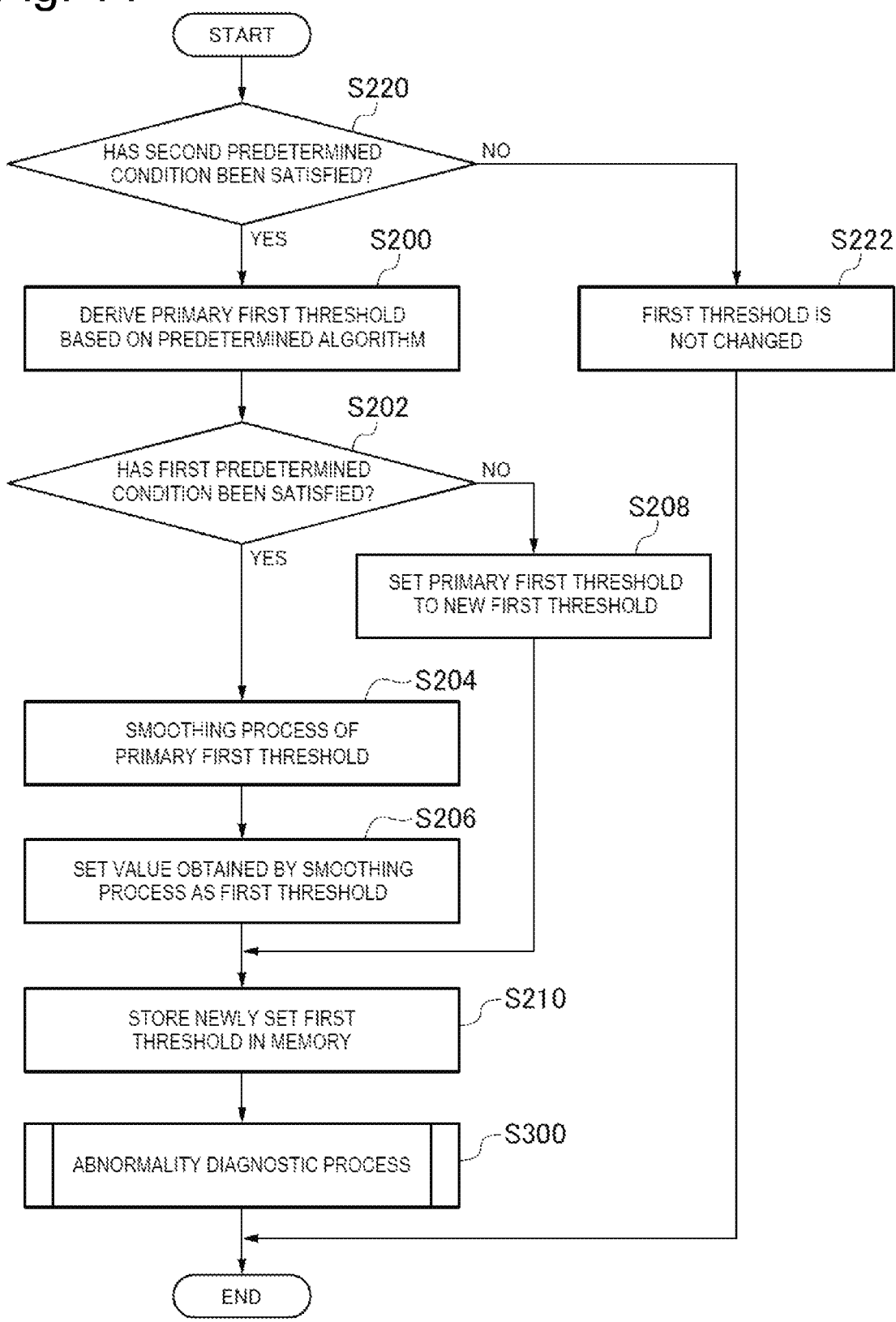
FIG. 14 is a flowchart illustrating another example of a threshold changing process.
Figure 15:
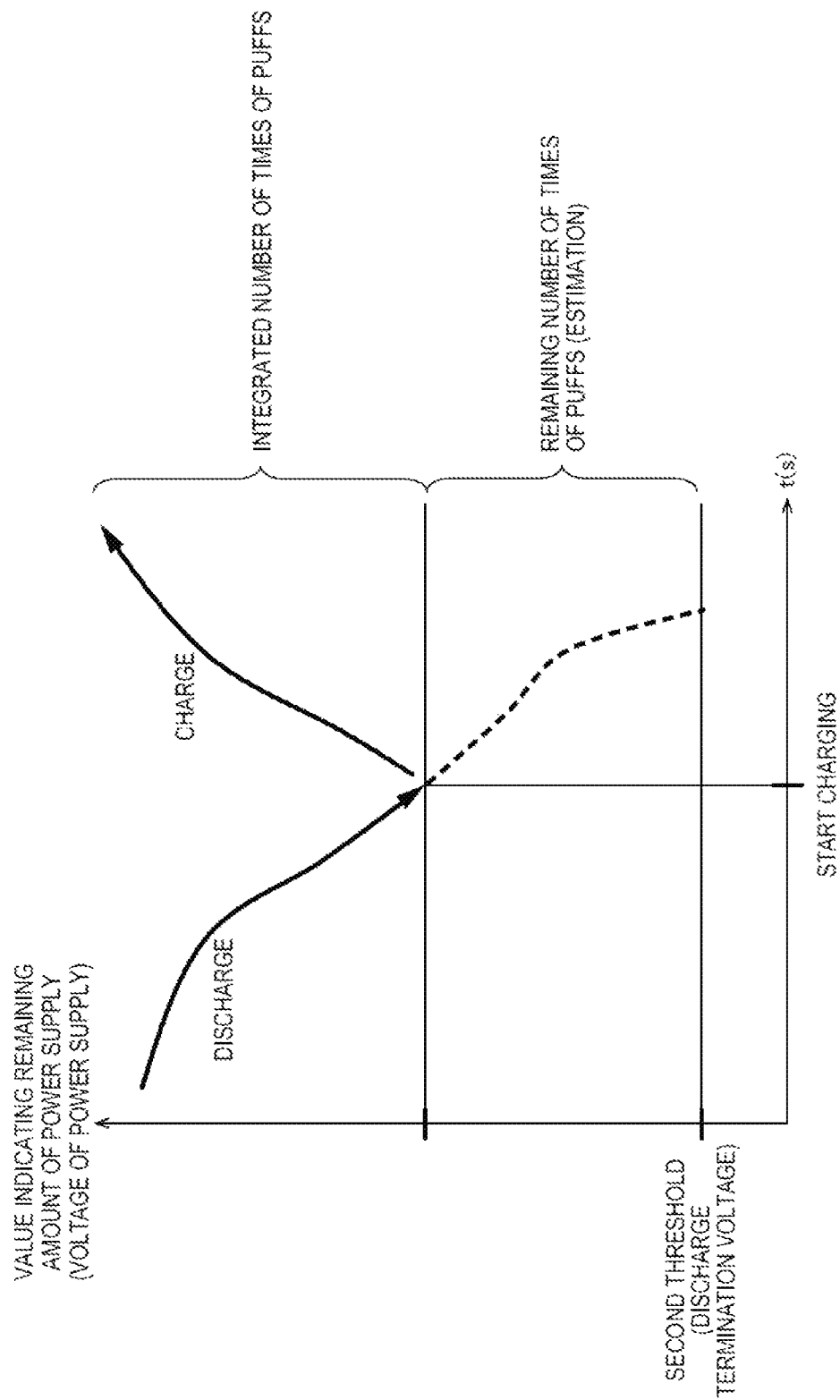
FIG. 15 is a graph showing a voltage value of the power supply when the voltage of the power supply starts charging before reaching a discharge termination voltage.

Another example of the threshold changing process will be described in detail. FIG. 14 illustrates an example of a flowchart of the threshold changing process. It is preferable that the control unit 50 performs the threshold changing process S104 when the power supply 10 is charged before the value indicating the remaining amount of the power supply 10 becomes less than the second threshold. Note that FIG. 15 shows the voltage value of the power supply when the voltage of the power supply 10 starts charging before reaching the second threshold, for example, the discharge termination voltage.

In the threshold changing process according to the present example, when the second predetermined condition is not satisfied, it is preferable to end the threshold changing process without changing the first threshold (steps S220 and S222).

In one aspect, the second predetermined condition is a condition that an operation amount of the load 121R or an amount of inhalation component generated by the load 121R at or before the start of the charging of the power supply 10 is equal to or more than a reference amount. That is, when the operation amount of the load 121R or the amount of inhalation component generated by the load 121R at or before the start of the charging of the power supply 10 is less than the reference amount, the first threshold is not changed. Here, the operation amount of the load 121R or the amount of inhalation component generated by the load 121R is calculated from the time when the charging was performed previously.

In another aspect, the second predetermined condition is a condition that the value acquired by the control unit 50 at or before the start of charging of the power supply 10 is less than the first threshold. That is, when the value indicating the remaining amount of the power supply 10 acquired by the control unit 50 at or before the start of charging of the power supply 10 is equal to or more than the first threshold, the first threshold is not changed. More specifically, when the value indicating the remaining amount of the power supply 10 is equal to or more than the first threshold, it is preferable that the first threshold is not changed even if the power supply 10 has been charged.

The second predetermined condition described above means a condition that the remaining amount of the power supply 10 is large, that is, the number of times of puff operations is small. Therefore, it is considered that the first threshold for distinguishing between the normal use mode and the charge request mode remains set to a relatively appropriate value without being changed.

In yet another aspect, the second predetermined condition is a condition that the neglect time period that is a period during which the electric power is not supplied to the load 121R is less than the predetermined time period. That is, the first threshold is not changed when the neglect time period that is a period during which the electric power is not supplied to the load 121R is equal to or more than the predetermined time period. The neglect time period can be measured by the timer 54 described above.

When the neglect time period increases beyond a predetermined time period, a significant voltage drop may occur due to natural discharge. Therefore, the accuracy of the threshold changing process, more specifically, the value of the primary first threshold value derived by the predetermined algorithm may decrease. When the first threshold is changed using such a primary first threshold, the first threshold for distinguishing between the normal use mode and the charge request mode may deviate from an appropriate value. Therefore, it is preferable not to change the first threshold in the case where a significant voltage drop occurs due to the natural discharge as described above.

In the threshold changing process, when the second predetermined condition is satisfied, the primary first threshold value is derived according to the predetermined algorithm (step S200). In the present example, the first threshold is changed based on a value larger than the second threshold by an amount corresponding to the amount of voltage drop of the power supply 10 when the load 121R is operated by an amount corresponding to the predetermined number of times. Here, the amount of voltage drop of the power supply 10 when the load 121R is operated by an amount corresponding to the predetermined number of times may be a value estimated by the control unit 50. That is, the amount of voltage drop of the power supply 10 is estimated based on the value indicating the remaining amount of the power supply 10 acquired by the control unit 50 at or before the start of charging of the power supply. That is, in the present example, the first threshold is changed to enable the puff operation to be performed about the predetermined number of times in the charge request mode.

Specifically, the control unit 50 acquires the voltage of the power supply 10 as a value indicating the remaining amount of the power supply 10 for each puff operation. Thus, the control unit 50 can acquire the voltage drop amount $\Delta V(i)$ for each puff operation. Here, "i" is an index indicating the number of times of puff operations.

When the power supply 10 is charged, the control unit 50 acquires the average value $_\Delta V_{AVE}$ of the voltage drop amount per puff operation. Here, the average value $_\Delta V_{AVE}$ of the voltage drop amount per puff operation may be calculated over the number of times of puff operations performed after the power supply 10 was charged previously.

Alternatively, the average value $_\Delta V_{AVE}$ of the voltage drop amount per puff operation may be calculated over the number of times of puff operations performed after the voltage of the power supply 10 falls below the predetermined value. In this case, the predetermined value may be the currently set first threshold. In this case, when charging of the power supply 10 is started before the voltage of the power supply 10 falls below the first threshold, the control unit 50 need not change the first threshold.

The control unit 50 uses the average value $_\Delta V_{AVE}$ of the voltage drop amount to estimate the remaining number of times of puffs at the start of charging. The remaining number of times of puffs is an index indicating how many more times of puff operations can be performed on the remaining amount of the power supply at the start of charging. The remaining number of times of puffs can be estimated, for example, by assuming that the voltage of the power supply 10 decreases linearly together with puff operation. In this case, the remaining number of times of puffs ($puff_{remain}$) can be obtained by the following equation: $puff_{remain}=(V(N)-\text{discharge termination voltage})/\Delta V_{AVE}$. Where V(N) means the voltage of the power supply 10 at the start of charging.

The control unit 50 acquires, from the memory 58, the voltage ($OCV(N+puff_{remain}-N_{re})$) of the power supply 10 acquired a predetermined number of times ($N_{re}$) before the sum of the number of times (N) of puff operations measured after the start of charging and the remaining number of times (puff$_{remain}$) of puffs using the remaining number of times puff$_{remain}$ of puffs thus estimated, and sets the acquired voltage as the primary first threshold.

As described above, when the first predetermined condition is not satisfied, the control unit 50 sets the primary first threshold to a new first threshold (steps S202 and S208). When the first predetermined condition is satisfied, the control unit 50 sets a value obtained by performing a smoothing process on the primary first threshold as the first threshold (steps S202, S204, and S206). Here, the first predetermined condition may be, for example, a condition that the state of health of the power supply 10 has not progressed beyond the predetermined determination state.

The predetermined number of times ($N_{re}$) is as described above, and may be a preset fixed value or a variable value that can be set by the user.

(Yet Another Example of Predetermined Algorithm)

Figure 16:
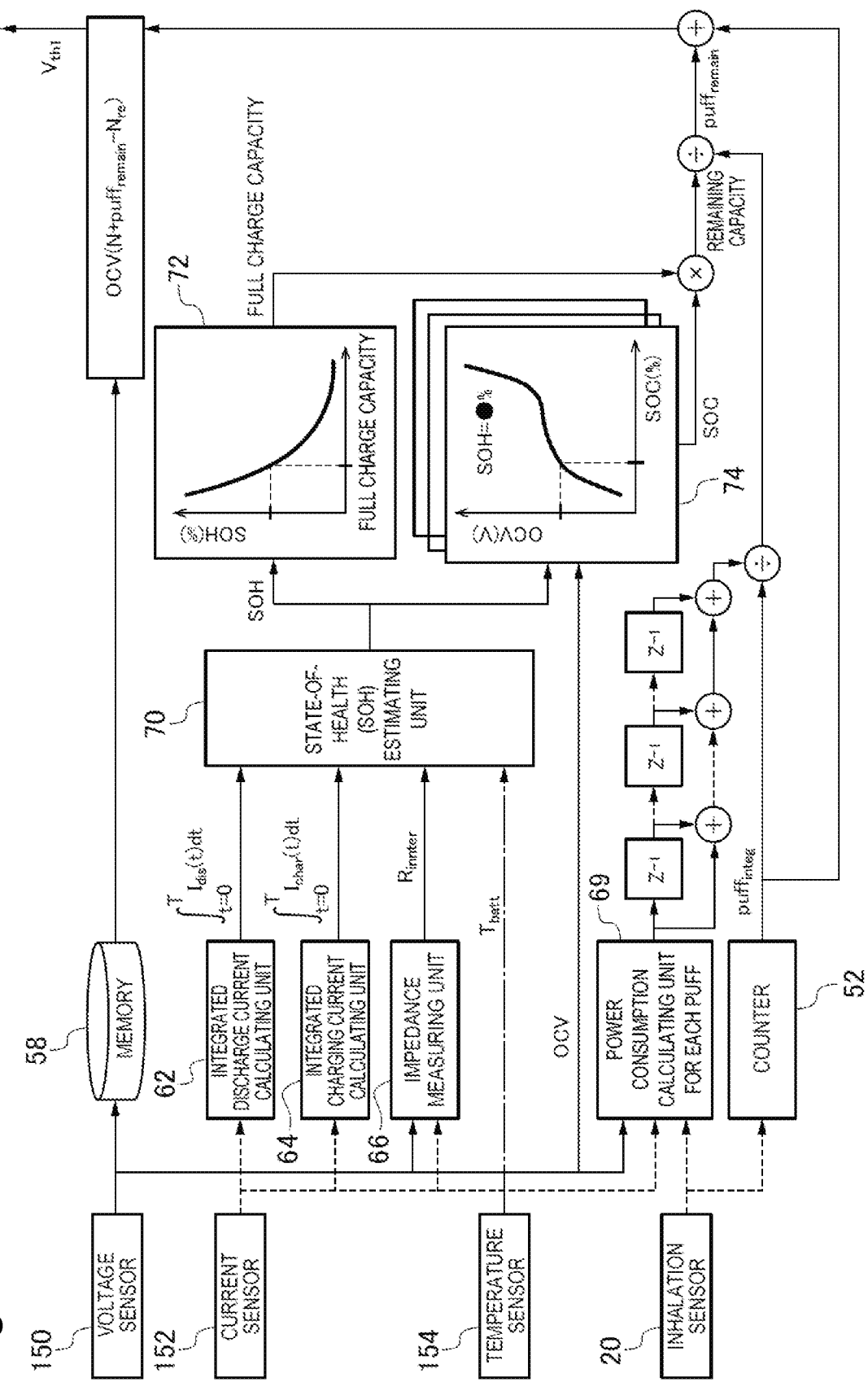
FIG. 16 illustrates another example of a block diagram of a control unit for performing a predetermined algorithm.

Next, yet another example of the predetermined algorithm will be described. FIG. 16 illustrates a block diagram of a control unit for performing a predetermined algorithm according to the present example.

In the example illustrated in FIG. 16, the value indicating the remaining amount of the power supply 10 is defined by the state of charge (SOC) or remaining capacity of the power supply 10. In this case, the second threshold may be the state of charge or remaining capacity of the power supply when the voltage of the power supply reaches the discharge termination voltage. Furthermore, in this case, in the flowchart illustrated in FIG. 7, the control unit 50 acquires the state of charge or remaining capacity of the power supply 10 as a value indicating the remaining amount of the power supply 10. The acquired state of charge or remaining capacity is stored in the memory 58 each time a puff operation is performed. When the state of charge (SOC) of the power supply 10 is used as a value indicating the remaining amount of the power supply 10, the second threshold in step S110 and the first threshold in step S116 are values suitable for comparison with the state of charge (SOC), and the dimension (unit) is (%). On the other hand, when the remaining capacity of the power supply 10 is used as a value indicating the remaining amount of the power supply 10, the first threshold in step S110 and the second threshold in step S116 are values suitable for comparison with the remaining capacity, and the dimension (unit) is (Wh).

It is preferable that the predetermined algorithm according to the present example is performed when the state of charge of the power supply 10 becomes equal to or less than the state of charge or remaining amount corresponding to the discharge termination voltage. In this algorithm, the first threshold is changed based on a value larger than the second threshold by an amount corresponding to the decrease amount of the state of charge or remaining capacity of the power supply 10 when the load 121R is operated by an amount corresponding to the predetermined number of times. The decrease amount of the state of charge or remaining capacity of the power supply 10 is estimated based on the state of charge or remaining capacity acquired by the control unit 50 at or before the start of charging of the power supply 10.

The state of charge (SOC) or remaining capacity of the power supply 10 can be estimated by, for example, a known SOC-OCV method, current integration method (coulomb counting method) or the like. FIG. 16 illustrates an example using the SOC-OCV method. In this method, the control unit 50 includes a state-of-health estimating unit 70 configured to estimate the state of health of the power supply 10. Furthermore, the control unit 50 includes an integrated discharge current calculating unit 62, an integrated charging current calculating unit 64, an impedance measuring unit 66, and a power consumption calculating unit 69 for each puff.

The integrated discharge current calculating unit 62 and the integrated charging current calculating unit 64 calculate the integrated value of the current flowing out of the power supply 10 and the integrated value of the current flowing into the power supply 10, respectively, using the current sensor 152. The impedance measuring unit 66 measures the impedance (internal resistance) using the voltage sensor 150 and the current sensor 152. The state-of-health estimating unit 70 acquires the state of health (SOH) of the power supply 10 based on the integrated value of the current flowing out of the power supply 10, the integrated value of the current flowing into the power supply 10, the impedance, and the temperature measured using the temperature sensor 154 by a known method.

The control unit 50 acquires the full charging capacity of the power supply 10 based on the state of health (SOH) of the power supply 10 by the mapping 72. In addition, the control unit 50 derives the state of charge (%) of the power supply 10 from the voltage value of the power supply 10 at the start of charging, using the appropriate mapping 74 based on the state of health (SOH) of the power supply 10. The control unit 50 can estimate the remaining capacity of the power supply 10 at the start of charging by multiplying the acquired full charge capacity and the state of charge (SOC) of the power supply 10.

Furthermore, the control unit 50 derives an estimate of the power consumption amount required for one puff operation by a value obtained by dividing the accumulated value of the power consumption amount for each puff derived by the power consumption calculating unit 69 for each puff by the number of times of puffs. The control unit 50 can estimate the remaining number of times (puff$_{remain}$) by dividing the remaining capacity of the power supply 10 at the start of charging by the estimate of the power consumption amount required for one puff operation.

The control unit 50 acquires, from the memory 58, the voltage (OCV(N+puff$_{remain}$−$N_{re}$)) of the power supply 10 acquired a predetermined number of times ($N_{re}$) before the sum of the number of times (N) of puff operations measured after the start of charging and the remaining number of times (puff$_{remain}$) of puffs using the remaining number of times puff$_{remain}$ of puffs thus estimated, and sets the acquired voltage as the primary first threshold.

As described above, when the first predetermined condition is not satisfied, the control unit 50 sets the primary first threshold to a new first threshold (steps S202 and S208). When the first predetermined condition is satisfied, the control unit 50 sets a value obtained by performing a smoothing process on the primary first threshold as the first threshold (steps S202, S204, and S206). Here, the first predetermined condition may be, for example, a condition that the state of health of the power supply 10 has not progressed beyond the predetermined determination state.

The predetermined number of times ($N_{re}$) may be a preset fixed value or a variable value that can be set by the user, as described above.

In the present example, the algorithm for deriving the open circuit voltage as a primary first threshold has been described in detail. Instead of this, when the state of charge (SOC) or remaining capacity of the power supply 10 is used as a value indicating the remaining amount of the power supply 10, the "state of charge or remaining capacity of the power supply 10 required for operating the load 121R by an amount corresponding to the predetermined number of times" that is derived in the previous stage of the mapping 74 illustrated in in FIG. 16 may be used as a primary first threshold. Alternatively, instead of this, the "state of charge or remaining capacity of the power supply 10 required for operating the load 121R by an amount corresponding to the predetermined number of times" that is derived using the mapping 74 or/and the full charging capacity, and the open circuit voltage derived by the mapping 74 may be used as a primary first threshold.

Furthermore, in the present example, although the algorithm for deriving the primary first threshold is different from the example described above, the threshold changing process can be performed as in the flowchart illustrated in FIG. 14, for example.

(Control by External Processor)

In the example described above, the control unit 50 performs all the processes of changing the first threshold according to a predetermined algorithm using the value indicating the remaining amount of the power supply 10. Alternatively, at least part of the processes may be performed by the processor 250 of the external power supply, for example, the processor of the charger 200.

As one example, the inhalation component generation device 100 may be communicable with a processor 250 of the external power supply capable of estimating the remaining amount of the power supply 10 at or before the start of discharge. The processor 250 can estimate the remaining amount of the power supply 10 at or before the start of charging of the power supply 10, and may transmit a value indicating the estimated remaining amount of the power supply 10 to the inhalation component generation device 100.

The processor 250 can estimate the remaining amount of the power supply 10 based on at least one of a value indicating the amount of electric power discharged from the power supply 10 to the external power supply 210 and a value indicating the amount of electric power charged from the external power supply 210 to the power supply 10. These amounts of electric power can be derived using the current sensor 230 and the voltage sensor 240.

The estimation of the remaining amount of the power supply 10 by the processor 250 may be performed by any known method. For example, when the power supply 10 is connected to the charger 200, the remaining amount of the power supply 10 can be estimated by the ratio between the discharged power amount when the power supply 10 is discharged to the discharge termination voltage and the charged power amount when the power supply 10 is charged from the discharge termination voltage to the fully charged voltage. In this case, the discharged power amount and the charged power amount can be derived, for example, by discharging the one-end power supply 10 to the discharge termination voltage and then charging it to the fully charged voltage.

When the processor 250 estimates the remaining amount of the power supply 10, the control unit 50 may change the first threshold based on the remaining amount of the power supply 10 acquired from the processor 250. Specifically, the control unit 50 can derive the primary first threshold by applying any of the above-described predetermined algorithms using the remaining amount of the power supply 10 acquired from the processor 250.

(Smoothing Process)

Figure 17:
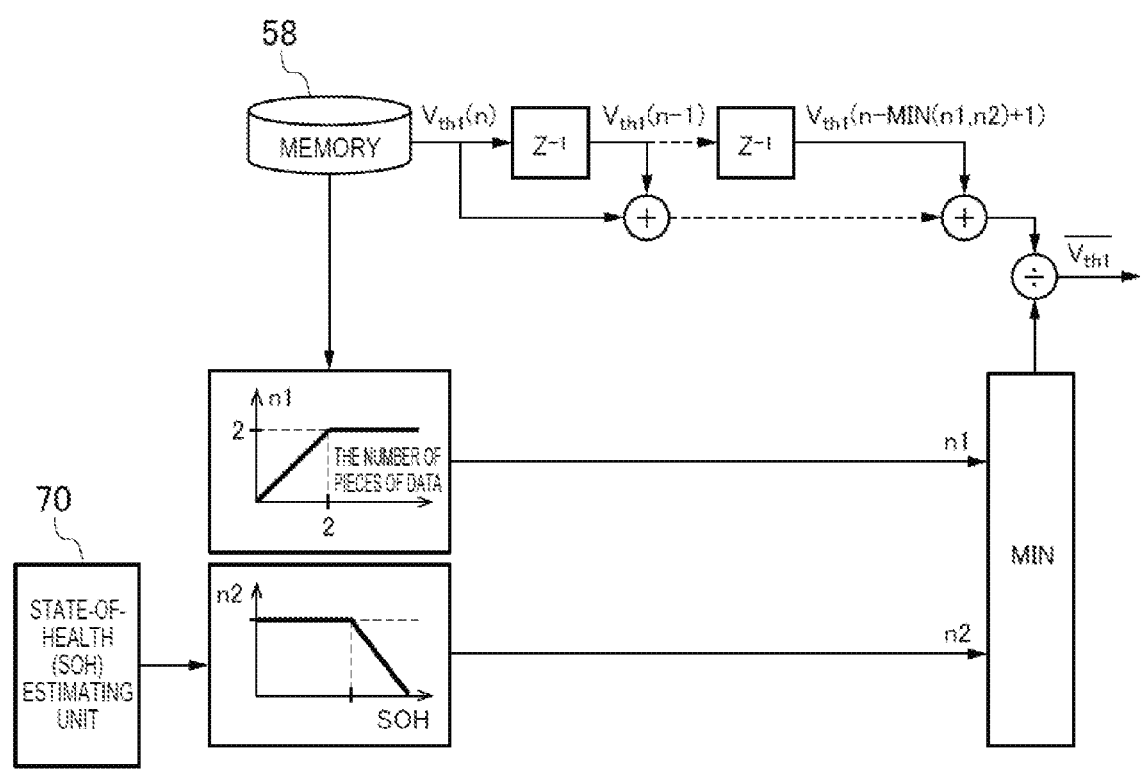
FIG. 17 illustrates an example of a block diagram of a control unit for performing the smoothing process.

FIG. 17 illustrates an example of a block diagram of a control unit for performing the smoothing process. The smoothing process may be, for example, a process of taking a moving average of a predetermined number of most recent first thresholds among a plurality of first thresholds changed in the past. That is, the smoothing process is a process of obtaining an average value of a predetermined number of first thresholds sequentially extracted from the newest one among the plurality of first thresholds ($V_{th1}$) stored in the memory 58.

As described above, the predetermined algorithm derives the primary first threshold based on the value of the voltage of the power supply 10. However, since the value of the voltage of the power supply 10 may include changes and errors due to various environments such as temperature conditions, simply setting the primary first threshold as the first threshold may cause the first threshold to be different from the previous first threshold. Setting a value obtained by performing the smoothing process on the primary first threshold as a new first threshold makes it possible to reduce changes and errors due to various environments such as temperature conditions. At the same time, it is possible to reduce the influence of the fine difference in the inhalation method for each inhalation by the user, the product error of the inhalation component generation device 100 and the change over time on the new first threshold. In addition, by suppressing a large change in the newly set first threshold, an unnatural feel sensed by the user can be prevented.

In an example, the intensity of the smoothing process may be changed based on the number of first thresholds that are previously changed, specifically, the number of first thresholds stored in the memory 58. For example, when the number of first thresholds already stored in the memory 58 is zero, the control unit 50 sets, as the first threshold, the primary first threshold derived by the predetermined algorithm without performing the smoothing process. That is, in this case, the number (n1) of first thresholds used for the smoothing process is zero.

In addition, when the number of first thresholds already stored in the memory 58 is one, the control unit 50 may set, as the first threshold, an average value of the first threshold stored in the memory 58 and the primary first threshold derived by a predetermined algorithm. That is, in this case, the number (n1) of first thresholds used for the smoothing process is one.

Furthermore, when the number of first thresholds already stored in the memory 58 is two or more, the control unit 50 may set, as the first threshold, an average value of two first thresholds stored in the memory and the primary first threshold derived by a predetermined algorithm. That is, in this case, the number (n1) of first thresholds used for the smoothing process is two.

Thus, the intensity of the smoothing process can be appropriately set by changing the number of values used to obtain the moving average according to the number of the first thresholds stored in the memory 58. As a result, it is possible to suppress the fact that the first threshold cannot be appropriately changed due to too strong smoothing process, and to suppress the fact that the process does not function due to too weak smoothing process.

Furthermore, the intensity of the smoothing process may be changed based on the state of health (SOH) of the power supply 10. Specifically, it is preferable that the intensity of the smoothing process is weakened as the state of health of the power supply 10 progresses. Specifically, as the state of health of the power supply 10 progresses, the number (n2) of first thresholds used for the smoothing process may be reduced. More preferably, the number of first thresholds used in the smoothing process may be a smaller one of the number (n1) according to the number of first thresholds stored in the memory 58 and the number (n2) obtained based on the state of health (SOH) of the power supply 10 (see FIG. 17).

For example, when the state of health (SOH) of the power supply 10 is equal to or less than the first determination state, the control unit 50 may set, as the first threshold, an average value of two first thresholds already stored in the memory 58 and the primary first threshold derived by a predetermined algorithm. However, when the number of first thresholds stored in the memory 58 is less than two, the number of first thresholds used for the smoothing process may be reduced according to the number of first thresholds stored in the memory 58. Similarly, when the first threshold is not stored in the memory 58, the smoothing process need not be performed.

In addition, when the state of health (SOH) of the power supply 10 progresses beyond the first determination state and is equal to or less than the second determination state, the control unit 50 sets, as the first threshold, an average value of one first threshold already stored in the memory 58 and the primary first threshold derived by a predetermined algorithm. However, when the first threshold is not stored in the memory 58, the smoothing process need not be performed.

Furthermore, when the state of health (SOH) of the power supply 10 progresses beyond the second determination state, it is preferable that the control unit 50 sets the first threshold to the primary first threshold derived by a predetermined algorithm (steps S202 and S208).

While the power supply 10 is degraded, the value indicating the remaining amount of the power supply 10, for example, the voltage of the power supply 10, the state of charge of the power supply 10, and the value of the remaining capacity of the power supply 10 may change rapidly. In such a case, it is possible to set the first threshold to a value reflecting the state of health of the power supply 10 in the threshold changing process by weakening the intensity of the smoothing process or not performing the smoothing process.

It is preferable that the control unit 50 uses only the first threshold obtained after the load 121R is attached to the connection unit 120t in the smoothing process. In addition, the control unit 50 may disable or delete at least a part, preferably all of the first thresholds stored in the memory 58 based on the attachment and detachment of the load 121R to and from the connection unit 120t. Thus, the control unit 50 can avoid using the first threshold obtained before the load 121R is attached to the connection unit 120t in the smoothing process.

Note that, in the present example, as the smoothing process for the primary first threshold, the process of taking the moving average of the primary first threshold and the first threshold stored in the memory 58 has been described in detail. Instead of this, it is possible to use a smoothing process of a plurality of first thresholds stored in the memory 58 or a smoothing process by least squares method of a data group obtained by adding the primary first threshold to the plurality of first thresholds. Alternatively, in the smoothing process, a weighted moving average or an exponential moving average may be performed such that more recent first thresholds stored in the memory 58 are weighted more heavily.

Furthermore, in the present example, an algorithm has been described in detail in which the primary first threshold derived in step S200 in FIG. 11 and FIG. 14 is not stored in the memory 58 and is regarded as a temporary variable in the control flow. Instead of this, the primary first threshold derived in step S200 of FIG. 11 and FIG. 14 may be stored in the memory 58 before the smoothing process is performed. That is, in FIG. 17, the newest data $V_{th1}(n)$ stored in the memory 58 becomes the primary first threshold derived in step S200 in FIG. 11 and FIG. 14 before the smoothing process is performed. Therefore, to set the intensity of the smoothing process based on the number of first thresholds stored in the memory 58 described above and the state of health (SOH) of the power supply 10, at least one piece of data is stored in the memory 58. In this case, in the smoothing process, it is necessary to increase the number (n1) according to the number of first thresholds stored in the memory 58 by 1 over all of the first thresholds stored in the memory 58. Similarly, it is necessary to increase the number (n2) obtained based on the state of health (SOH) of the power supply 10 by 1 over the entire state of health (SOH) of the power supply 10. Furthermore, it should be noted that the primary first threshold value $V_{th1}(n)$ stored in the memory 58 should be overwritten with the new first threshold obtained by the smoothing process.

Furthermore, in the present example, the smoothing process in the case where the voltage of the power supply 10 is used as the value indicating the remaining amount of the power supply 10, the primary first threshold and the first threshold has been described in detail. Instead of this, the state of charge (SOC) and remaining capacity of the power supply 10 may be used as the value indicating the remaining amount of the power supply 10, the primary first threshold and the first threshold.

(Measures Against Prolonged Neglect)

If the above-described threshold changing process is performed after the prolonged neglect of the power supply 10, the accuracy of the above-described predetermined algorithm may decrease due to the natural discharge. Therefore, it is preferable that the control unit 50 corrects the first threshold that is changed based on the operation request signal according to the neglect time period. Here, the neglect time period is defined by a period in which the electric power is not supplied to the load 121R as described above, and can be measured by the timer 54.

Figure 18:
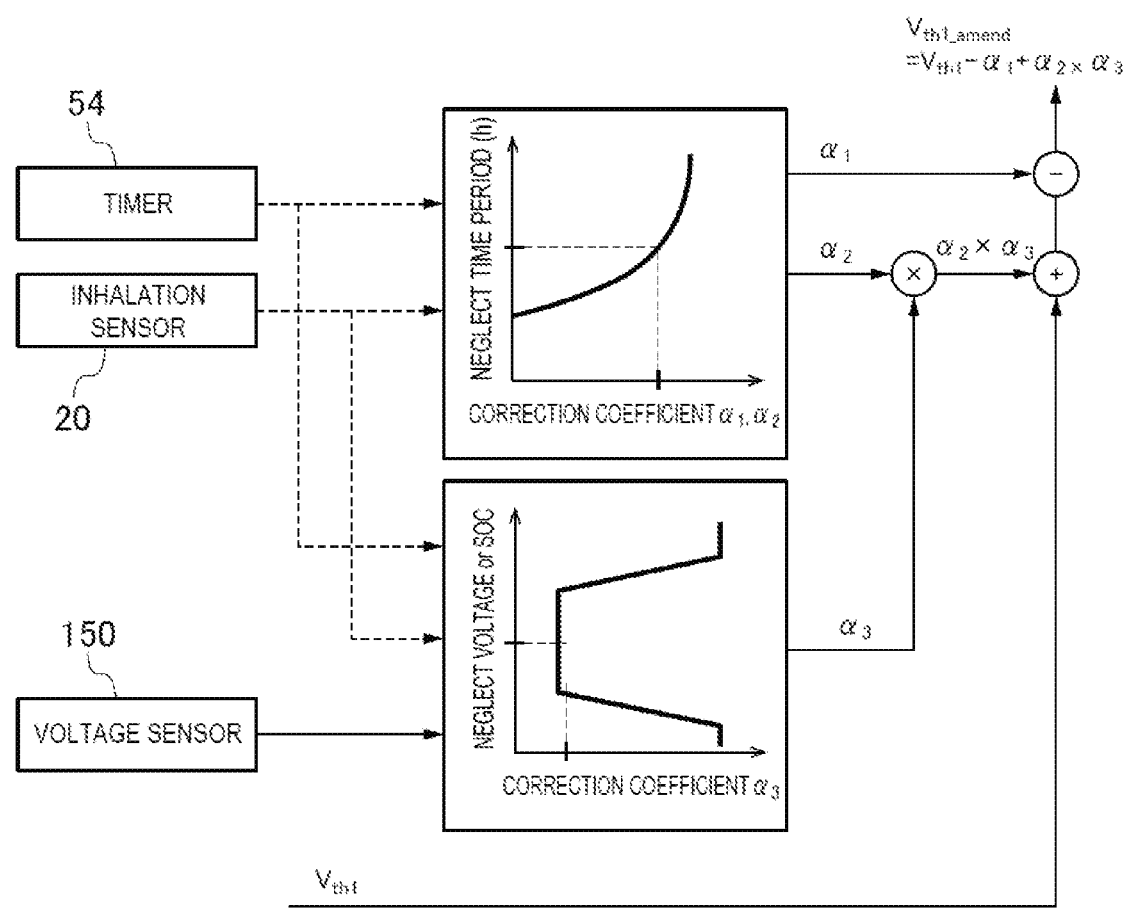
FIG. 18 illustrates an example of a block diagram of a control unit for performing a correction of the first threshold in the case of performing the threshold changing process after the prolonged neglect.

FIG. 18 illustrates an example of a block diagram of a control unit for performing the correction of the first threshold in the case of performing the threshold changing process after the prolonged neglect. In the present example, the control unit 50 corrects the primary first threshold ($V_{th1}$) derived by the predetermined algorithm according to the following correction equation: $V_{th1\_amend} = V_{th1} - \alpha1 + \alpha2 \times \alpha3$.

Here, $V_{th1\_amend}$ is a primary first threshold after correction. "$V_{th1}$" is a primary first threshold before correction, that is, a primary first threshold obtained by the above-described predetermined algorithm. "α1," "α2" and "α3" are correction coefficients respectively.

The correction coefficient α1 is a coefficient for compensating for the natural drop of the voltage of the power supply 10 accompanying the neglect of the power supply 10. According to the above-described predetermined algorithm, when the correction according to the neglect time period is not performed, the primary first threshold may be set to a value higher by a voltage drop due to the natural discharge. Therefore, the correction coefficient α1 may be set to cancel the voltage drop due to the natural discharge. That is, it is preferable that the control unit 50 corrects the primary first threshold value to a smaller value according to the neglect time period.

The correction coefficients α2 and α3 are coefficients for compensating for the capacity deterioration of the power supply 10 (in other words, the decrease of the full charge capacity) accompanying the neglect of the power supply 10. In general, it is known that the degradation of the power supply 10 progresses due to the prolonged neglect, and the full charge capacity decreases. Furthermore, the degree of this decrease depends on the remaining amount of the power supply 10 at the time of neglect. According to the above-described predetermined algorithm, the primary first threshold may be set to a lower value by a decrease in the full charge capacity when correction is not performed according to the neglect time period. Therefore, it is preferable to perform the correction based on the correction coefficients α2 and α3 in consideration of the decrease in the full charge capacity accompanying the prolonged neglect.

The correction coefficient α3 is a value corresponding to the remaining amount of the power supply 10 when the load 121R operates or generates an inhalation component. More specifically, the correction coefficient α3 is a value corresponding to the remaining amount of the power supply 10 when the load 121R is operated after the neglect of the power supply 10. As described above, the decrease in the full charge capacity of the power supply 10 due to the prolonged neglect depends on the remaining amount of the power supply at the time of neglect. In particular, when the power supply 10 is subject to the prolonged neglect with about remaining amount corresponding to the fully charged voltage or the discharge termination voltage, the full charge capacity of the power supply 10 is likely to decrease. From this point of view, it is preferable to correct the primary first threshold to a larger value as the remaining amount of the power supply 10 at the time of neglect is closer to the fully charged voltage or the discharge termination voltage.

And the decrease in the electrical storage capacity (≈ the possible number of times of puff operations) accompanying the neglect of the power supply 10 is influenced also by the length of neglect time period. Therefore, the control unit 50 may correct the primary first threshold by adding, to the primary first threshold, the product of the correction coefficient α2 and the correction coefficient α3 based on the remaining amount of the power supply 10 at the time of neglect.

Note that the relationship between the correction coefficients α1 and α2 and the neglect time period is determined by the type (design) of the power supply 10 used. Similarly, the relationship between the correction coefficient α3 and the discharge voltage, the state of charge or remaining capacity of the power supply is determined by the type (design) of the power supply 10 used. Therefore, the correction coefficients α1, α2, and α3 can be derived by experiment in advance for the power supply 10 to be used.

The control unit 50 sets the value thus corrected as the first threshold. In addition, as described above, the value obtained by performing the smoothing process on the value thus corrected may be set as the first threshold.

Furthermore, in the present example, the smoothing process in the case where the voltage of the power supply 10 is used as the value indicating the remaining amount of the power supply 10, the primary first threshold and the first threshold has been described in detail. Instead of this, the state of charge (SOC) or remaining capacity of the power supply 10 may be used as the value indicating the remaining amount of the power supply 10, the primary first threshold and the first threshold.

(Abnormality Determination Process)

Figure 19:
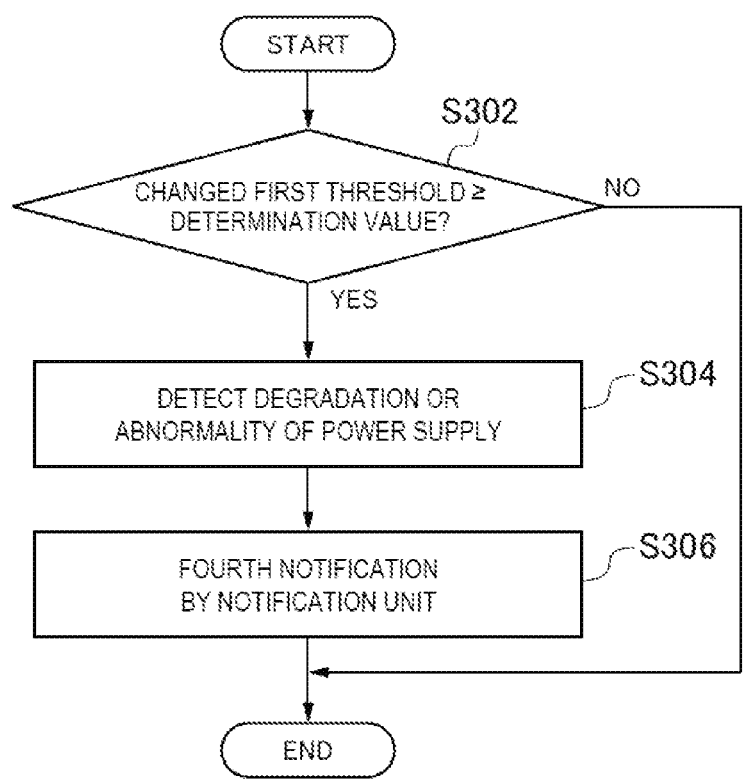
FIG. 19 is a flowchart illustrating an example of an abnormality determination process.

FIG. 19 is a flowchart illustrating an example of an abnormality determination process. The control unit 50 detects degradation or abnormalities of the power supply 10, when the changed first threshold is equal to or more than a predetermined determination value (step S302).

In the degraded power supply 10, the value indicating the remaining amount of the power supply 10 decreases rapidly together with the number of times of puff operations. Therefore, when it is attempted to change the first threshold based on a value capable of operating the load 121R or generating the inhalation component by an amount corresponding to the predetermined number of times, the first threshold increases together with the degradation of the power supply 10. Therefore, when the changed first threshold is equal to or more than the predetermined determination value, it can be considered that the power supply 10 has been degraded or an abnormality has occurred in the power supply 10.

Here, the predetermined determination value may be set to a predetermined value that may be considered as degradation of the power supply 10 or abnormality of the power supply 10. When the value indicating the remaining amount of the power supply 10 is the voltage of the power supply 10 and a lithium ion secondary battery is used as the power supply 10, the predetermined determination value may be, for example, in the range of 3.7 to 3.9 V.

The control unit 50 controls the notification unit 40 to perform fourth notification when the degradation or the abnormality of the power supply 10 has been detected (step S306). It is preferable that the fourth notification is different from the first notification, the second notification, and the third notification described above. When the notification unit 40 is a light emitting element, the light emission color and/or light emission pattern of the light emitting element in the fourth notification are different from the light emission color and/or light emission pattern of the light emitting element in each of the first notification, the second notification and the third notification.

The control unit 50 may stop any operation of the inhalation component generation device 100 when detecting an abnormality.

OTHER EMBODIMENTS

Although the present invention has been described by the embodiments described above, it should not be understood that the descriptions and the drawings that form a part of this disclosure limit the present invention. Various alternative embodiments, examples and operation techniques will be apparent to those skilled in the art from this disclosure.

For example, configurations described in each of the above-described embodiments may be combined and/or rearranged as much as possible.

Furthermore, it should be noted that a program for causing the inhalation component generation device to execute various methods described above that are performed by the control unit 50 is also included in the scope of the present invention.

The invention claimed is:

1. An inhalation component generation device, comprising:
 a load configured to vaporize or atomize an inhalation component source with electric power from a power supply;

a user interface; and a circuitry configured to acquire a value indicating a remaining amount of the power supply and acquire an operation request signal to the load to generate a command for operating the load;

cause the user interface to perform first notification in a case that the value indicating the remaining amount of the power supply is less than a first threshold and equal to or more than a second threshold smaller than the first threshold;

cause the user interface to perform second notification in a case that the value indicating the remaining amount of the power supply is less than the second threshold, wherein the first threshold is changeable based on an algorithm, wherein the algorithm is performed i) in response to the voltage of the power supply being equal to or lower than a discharge termination voltage of the power supply or ii) in response to the state of charge of the power supply becoming equal to or less than the state of charge or remaining amount corresponding to the discharge termination voltage, and the circuitry is configured to perform a smoothing process by which a primary first threshold derived by the algorithm approaches at least one of a plurality of the first thresholds that are previously changed and set the first threshold based on a value derived by the smoothing process.

2. The inhalation component generation device of claim 1, wherein an intensity of the smoothing process is changed based on the number of the first thresholds that are previously changed.

3. The inhalation component generation device of claim 1, wherein the number of the first thresholds used for the smoothing process is changed based on the number of the first thresholds that are previously changed.

4. The inhalation component generation device of claim 1, wherein the circuitry is configured to acquire a state of health of the power supply, and the intensity of the smoothing process is changed based on the state of health.

5. The inhalation component generation device of claim 4, wherein the number of the first thresholds used for the smoothing process is changer based on the state of health.

6. The inhalation component generation device of claim 4, wherein the intensity of the smoothing process is weakened as the state of health progresses.

7. The inhalation component generation device of claim 4, wherein the circuitry is configured to set the first threshold to a primary first threshold derived by the predetermined algorithm in a case that the state of health has progressed beyond a predetermined determination state.

8. The inhalation component generation device of claim 4, wherein the circuitry is configured to acquire a stale of health of the power supply, and the intensity of the smoothing process is changed based on the number of the first thresholds that are previously changed and the state of health weighted by the number of the first thresholds.

9. The inhalation component generation device of claim 8, wherein the number of the first thresholds used in the smoothing process is changed based on the number of the first thresholds that are previously changed and the state of health weighted by the number of the first thresholds.

10. The inhalation component generation device of claim 1, wherein the circuitry is configured to detect degradation or abnormalities of the power supply in a case that the set first threshold is equal to or more than a predetermined determination value.

11. The inhalation component generation device of claim 10, wherein the circuitry is configured to control the user interface to perform a third notification in a case that the degradation or abnormality of the power supply has been detected.

12. The inhalation component generation device of claim 1, further comprising:

a connector configured to electrically disconnect and connect the load from/to the power supply, wherein the circuitry is configured to use only the first threshold obtained after the load is attached to the connector in the smoothing process.

13. The inhalation component generation device of claim 1, further comprising:

a memory configured to store a history of the first threshold; and a connector configured to electrically disconnect and connect the load from/to the power supply, wherein the circuitry is configured to disable or delete at least a part of the first thresholds stored in the memory based on attachment and detachment of the load to and from the connector.

14. The inhalation component generation device of claim 1, wherein the circuitry is configured to change the first threshold in a case that a value indicating a remaining amount of the power supply is equal to or less than the second threshold or the power supply is charged.

* * * * *